(12) United States Patent
Grelier et al.

(10) Patent No.: US 10,155,969 B2
(45) Date of Patent: Dec. 18, 2018

(54) PROCESS FOR PREPARING BIPHENYL COMPOUNDS

(71) Applicants: UNIVERSITÉ DE BORDEAUX, Bordeaux (FR); INSTITUT POLYTECHNIQUE DE BORDEAUX, Talence (FR); Centre national de la recherche scientifique (C.N.R.S), Paris (FR)

(72) Inventors: Stéphane Grelier, Parentis-en born (FR); Henri Cramail, Sainte Terre (FR); Audrey Llevot, Bordeaux (FR); Stéphane Carlotti, Pessac (FR); Etienne Grau, Talence (FR)

(73) Assignees: UNIVERSITE DE BORDEAUX, Bordeaux (FR); INSTITUTE POLYTECHNIQUE DE BORDEAUX, Talence (FR); CENTRE NATIONAL DE LA RECHERCHE SCIENTIFIQUE (C.N.R.S), Paris (FR)

( * ) Notice: Subject to any disclaimer, the term of this patent is extended or adjusted under 35 U.S.C. 154(b) by 0 days.

(21) Appl. No.: 15/516,318

(22) PCT Filed: Oct. 5, 2015

(86) PCT No.: PCT/EP2015/072957
§ 371 (c)(1),
(2) Date: Mar. 31, 2017

(87) PCT Pub. No.: WO2016/050988
PCT Pub. Date: Apr. 7, 2016

(65) Prior Publication Data
US 2017/0240937 A1 Aug. 24, 2017

(30) Foreign Application Priority Data
Oct. 3, 2014 (EP) .................... 14306566

(51) Int. Cl.
| | | |
|---|---|---|
| C07C 39/00 | (2006.01) |
| C12P 13/00 | (2006.01) |
| C07C 255/54 | (2006.01) |
| C07C 69/94 | (2006.01) |
| C07C 43/215 | (2006.01) |
| C12P 7/22 | (2006.01) |
| C12P 7/24 | (2006.01) |
| C12P 7/26 | (2006.01) |
| C12P 7/62 | (2006.01) |
| C12P 7/66 | (2006.01) |
| C07C 67/08 | (2006.01) |
| C07C 67/31 | (2006.01) |
| C07C 67/343 | (2006.01) |
| C07C 41/16 | (2006.01) |
| C07C 41/26 | (2006.01) |
| C07C 41/30 | (2006.01) |
| C07C 45/71 | (2006.01) |
| C07C 51/09 | (2006.01) |
| C07C 253/30 | (2006.01) |
| C07D 303/27 | (2006.01) |

(Continued)

(52) U.S. Cl.
CPC ............ *C12P 13/002* (2013.01); *C07C 41/16* (2013.01); *C07C 41/26* (2013.01); *C07C 41/30* (2013.01); *C07C 43/215* (2013.01); *C07C 45/71* (2013.01); *C07C 51/09* (2013.01); *C07C 67/08* (2013.01); *C07C 67/31* (2013.01); *C07C 67/343* (2013.01); *C07C 69/94* (2013.01); *C07C 253/30* (2013.01); *C07C 255/54* (2013.01); *C07D 303/27* (2013.01); *C07D 303/28* (2013.01); *C12P 7/00* (2013.01); *C12P 7/22* (2013.01); *C12P 7/24* (2013.01); *C12P 7/26* (2013.01); *C12P 7/44* (2013.01); *C12P 7/62* (2013.01); *C12P 7/66* (2013.01); *C12Y 110/03002* (2013.01)

(58) Field of Classification Search
CPC ........ C07C 67/343; C07C 67/08; C07C 67/31
USPC .......................................... 568/717
See application file for complete search history.

(56) References Cited

PUBLICATIONS

Lahtinen, J. Agric Food Chem. 2009, 8357-8365.*
(Continued)

*Primary Examiner* — Ana Z Muresan
(74) *Attorney, Agent, or Firm* — B. Aaron Schuman, Esq.; Stites & Harbison, PLLC

(57) ABSTRACT

The present invention relates to a process for preparing a compound having the formula (I), said process comprising the following steps: a) the addition of an oxygen source into a solution of a compound of formula (II), in a water-miscible solvent, b) the addition of a laccase in the solution obtained after step a); and c) the possible recovering of the compound of formula (I) thus obtained.

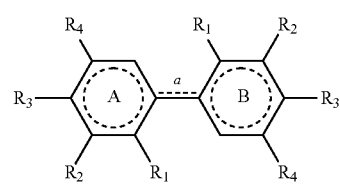

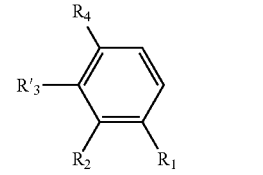

13 Claims, No Drawings

(51) Int. Cl.
C07D 303/28 (2006.01)
C12P 7/00 (2006.01)
C12P 7/44 (2006.01)

(56) References Cited

PUBLICATIONS

Maarit Lahtinen et al: "On the Reactions of Two Fungal Laccases Differing in Their Redox Potential with Lignin Model Compounds: Products and Their Rate of Formation", Journal of Agricultural and Food Chemistry, vol. 57, No. 18, Sep. 23, 2009 (Sep. 23, 2009), pp. 8357-8365, XP055178091, ISSN: 0021-8561, DOI: 10.1021/jf901511k * abstract; figure 2; tables 2-4; compounds 1, 9 * * p. 8358, right-hand column, paragraphs 2, 5*.

Mihaela-Anca Constantin et al: "Laccase-catalyzed oxidative phenolic coupling of vanillidene derivatives", Green Chemistry, vol. 14, No. 9, Jan. 1, 2012(Jan. 1, 2012), pp. 2375-2379, XP055178175, ISSN: 1463-9262, DOI: 10.1039/c2gc35848d * p. 2376, right-hand column, paragraph 2; tables 1-3 *.

F Tiemann: "Ueber eine charakteristische Reaction des Vanillins", Berichte Der Deutschen Chemischen Gesellschaft, vol. 18, Jan. 1, 1885(Jan. 1, 1885), pp. 3493-3496, XP055178398, DOI: 10.1002/cber.188501802336 * p. 3493, paragraph 2-p. 3494, paragraph 2 *.

Machado A E H et al: "Photocatalytic Degradation of Lignin and Lignin Models, Using Titanium Dioxide: The Role of the Hydroxyl Radical", Chemosphere, Pergamon Press, Oxford, GB, vol. 40, No. 1, Jan. 1, 2000 (Jan. 1, 2000), pp. 115-124, XP001024191, ISSN: 0045-6535, DOI: 10.1016/S0045-6535(99)00269-6 * p. 116, right-hand column, paragraph 2 *.

Louis M. M. Mouterde et al: "Chemoenzymatic Total Synthesis of a Naturally Occurring (5-5')/(8'-0-4") Dehydrotrimer of Ferulic Acid", European Journal of Organic Chemistry, vol. 2013, No. 1, Jan. 26, 2013 (Jan. 26, 2013), pp. 173-179, XP055178082, ISSN: 1434-193X, DOI: 10.1002/ejoc.201201290 * abstract * * scheme 2; p. 175 * * p. 173, right-hand column, paragraph 2 * * p. 176, left-hand column, last paragraph—right-hand column, paragraph 1*.

Bollag J-M et al: "Enzymatic oligomerization of vanillic acid", Soil Biology and Biochemistry, Pergamon, Oxford, GB, vol. 14, No. 2, Jan. 1, 1982 (Jan. 1, 1982), pp. 157-163, XP023672060, ISSN: 0038-0717, DOI: 10.1016/0038-0717(82)90060-8 [retrieved on Jan. 1, 1982 * abstract; figures 3, 5; table 3 * * p. 159, right-hand column, paragraph 1-3 * * p. 157, right-hand column, paragraph 2-3 *.

R F Chapman et al: "Studies related to the Chemistry of Melanins. Part V W Attempts to Sy n t hesise H yd roxy lat ed B i-i ndol y ls, B i phen y l s, a nd l ndo l i ne-2-ca r boxy l is Acid as Possible Intermediates in the Formation of Melanins from 3,4=Di= hydroxyphenethylamine and 3,4-Dihydroxyphenylalanine", Journal of the Chemical Society C: Organic, vol. 1970, No. 6, Jan. 1, 1970 (Jan. 1, 1970), pp. 865-872, XP055195932, DOI: 10.1039/J39700000865 * p. 868, left-hand column, paragraph 6 *.

Hermann Richtzenhain: "Enzymatische Versuche zur Entstehung des Lignins, IV. Mitteil.: Dehydrierungen in der Guajacolreihe", Chemische Berichte, vol. 82, No. 6, Dec. 1, 1949 (Dec. 1, 1949), pp. 447-453, XP055178007, ISSN: 0009-2940, DOI: 10.1002/cber.19490820602 * abstract * * p. 447, last paragraph-p. 448, paragraph 1; compounds I-III, VIII-X * * Chapter "Beschreibung der Versuche"; p. 450-p. 451 *.

Karl Freudenberg et al: "Die an der Verholzung beteiligten Enzyme. Die Dehydrierung des Sinapinalkohols", Chemische Berichte, vol. 91, No. 3,Mar. 1, 1958(Mar. 1, 1958), pp. 581-590, XP055178166, ISSN: 0009-2940, DOI: 10.1002/cber.19580910317 * abstract * * p. 582 *.

Tadahiro Shiba et al: "Oxidation of isoeugenol and coniferyl alcohol catalyzed by laccases isolated from Rhus vernicifera Stokes and Pycnoporus coccineus", Journal of Molecular Catalysis B: Enzymatic, vol. 10, No. 6, Nov. 1, 2000 (Nov. 1, 2000), pp. 605-615, XP055178259, * abstract; figure 4; table 1*.

Qing Jiang et al: "Cobalt(II)-Porphyrin-Catalyzed Aerobic Oxidation: Oxidative Coupling of Phenols", European Journal of Organic Chemistry, vol. 2013, No. 10, Apr. 20, 2013(Apr. 20, 2013), pp. 1861-1866, XP055145107, ISSN: 1434-193X, DOI: 10.1002/ejoc.201201595 * abstract; table 2; compounds 1, 3, 10 *.

Database WPI Week 200574 Oct. 13, 2005 (Oct. 13, 2005) Thomson Scientific, London, GB; AN 2005-717420 XP002740960, & JP 2005 278571 A (Dainippon Ink & Chem Inc) Oct. 13, 2005 (Oct. 13, 2005) * abstract * * paragraphs [0009], [0024], [0028] *.

Annett Mikolasch et al: "Fungal laccases as tools for the synthesis of new hybrid molecules and biomaterials", Applied Microbiology and Biotechnology, Springer, Berlin, DE, vol. 82, No. 4, Jan. 30, 2009 (Jan. 30, 2009), pp. 605-624, XP019705513, ISSN: 1432-0614 * figure 2; table 1 *.

A. Llevot et al: "ADMET polymerization of bio-based biphenyl compounds", Polymer Chemistry, vol. 6, No. 44, Sep. 10, 2015 (Sep. 10, 2015), pp. 7693-7700, XP055235409, GB ISSN: 1759-9954, DOI: 10.1039/C5PY01232E abstract; compounds 1, 5, 9, 13, P1 scheme 1; p. 7694.

Audrey Llevot et al: "Renewable (semi)aromatic polyesters from symmetrical vanillin-based dimers", Polymer Chemistry, vol. 6, No. 33, Jul. 3, 2015(Jul. 3, 2015), pp. 6058-6066, XP055235410, GB SSN: 1759-9954, DOI: 10.1039/C5PY00824G abstract; compounds 1-4, P1 schemes 1 and 2; p. 6059.

Ananda S Amarasekara et al: "Vanillin based polymers: I. An electrochemical route to polyvanillin", Green Chemistry, vol. 14, Jan. 1, 2012 (Jan. 1, 2012), pp. 2395-2397, XP002737198, DOI: 10.1039/C2GC35645G abstract; figure 1.

Li et al, "Synthesis of Vanillin from Glucose", 1998, pp. 10545-10546, vol. 120, J. Am. Chem. Soc.

* cited by examiner

PROCESS FOR PREPARING BIPHENYL COMPOUNDS

The present invention concerns a new process for preparing biphenyl compounds.

Aromatic compounds constitute basic chemicals to manufacture everyday life items. Indeed, they play a key role in pharmaceutical, perfumes, dyestuff and polymer industries. In plastic industry, aromatic units offer rigidity, hydrophobicity and fire resistance to the derived polymers. Aromatic polyesters, such as poly(alkyleneterephtalate)s are widely commercially used, especially in food packaging and textile field due to their good thermomechanical properties. Aromatic polyamides, such as Kevlar constitute high performance polymers thanks to their high stability and rigidity. Finally, phenolic compounds constitute a widely used raw material. For instance, Bisphenol A is an important monomer for the synthesis of polycarbonates, epoxy resins and a popular plasticizer for thermoplastic polymers. These compounds are mainly petroleum based and derived from benzene, xylene and toluene.

Some aromatic structures can be synthesized from natural compounds or are directly found in nature but in limited quantity. The main source of phenolic compound and so aromatic compounds is lignin, isolated from wood or annual plant, and constitute the second most abundant renewable polymer after cellulose. Vanillin, phenol commercially available, can be extracted from lignin and also obtained by biosynthetic pathway from abundant glucose (K. Li and J. W. Frost, *Journal of the American Chemical Society*, 1998, 120, 10545-10546).

Another way to synthesize bisaromatic compounds is to dimerize lignin derivatives. Dehydrodivanillin is important as flavouring agent, antioxidant agent, or in food and cosmetic industry and was even used in microlithography. It has been synthesized by oxidative coupling using $FeCl_3$ or sodium/potassium persulfate or enzymatically with peroxidases using between 1 000 and 2 000 units of enzyme.

Environmental concerns and petrol depletions lead the plastic industry to find biobased aromatic alternatives.

Furthermore, the phenolic products as obtained with the known processes as mentioned above are not suitable as they do not have a sufficient purity and thus cannot be used in subsequent polymerization processes.

The aim of the present invention is thus to provide a process for the preparation of phenolic compounds with a good yield, preferably greater than 85%.

Another aim of the present invention is to provide a process for obtaining phenolic dimers with high purity, said dimers being suitable for subsequent polymerization.

Another aim of the present invention is to provide a green process for preparing phenolic compounds.

Therefore, the present invention relates to a process for preparing a compound having the following formula (I):

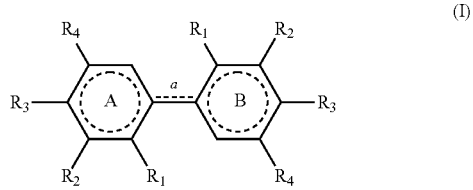

wherein:
$R_1$ is H or OH;
$R_2$ is a $(C_1-C_6)$alkoxy group;
$R_3$ is H or forms a C=O group with the carbon atom carrying it;
$R_4$ is R or R';

R being chosen from the group consisting of: —CHO, —CN, —$COR_a$, —$COOR_a$, —$R_a$, and $(C_2-C_6)$alkenyl groups, $R_a$ being a $(C_1-C_6)$alkyl group;
R' being a $(C_1-C_6)$alkoxy group;
and wherein, when the bond 'a' linking the cores A and B is a single bond, then the compound of formula (I) has the following formula (I-1):

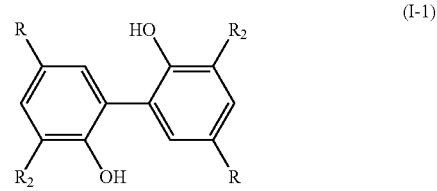

and when the bond 'a' linking the cores A and B is a double bond, then the compound of formula (I) has the following formula (I-2):

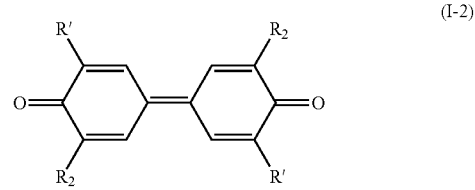

said process comprising the following steps:
a) the addition of an oxygen source into a solution of a compound of formula (II) in a water-miscible solvent, said compound of formula (II) having the following formula:

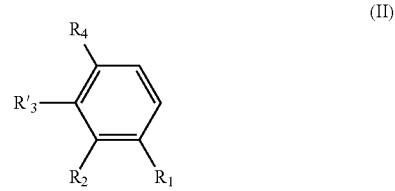

wherein $R_1$, $R_2$, and $R_4$ are as defined above in formula (I), and $R'_3$ is H when $R_1$ is OH and $R'_3$ is OH when $R_1$ is H,
b) the addition of a laccase in the solution obtained after step a); and
c) the possible recovering of the compound of formula (I) thus obtained.

The present invention also relates to a process for preparing a compound having the above-mentioned formula (I-1) wherein step a) is carried out with a compound having the following formula (II-1):

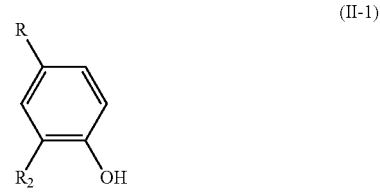

wherein R and $R_2$ are as defined above in formula (I).

The present invention thus also relates to a process for preparing a compound having the following formula (I-1):

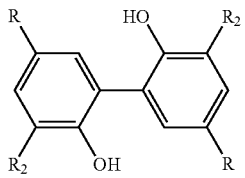

wherein:
R$_2$ is a (C$_1$-C$_6$)alkoxy group;
R is chosen from the group consisting of: —CHO, —CN, —COR$_a$, —COOR$_a$, —R$_a$, and (C$_2$-C$_6$)alkenyl groups, R$_a$ being a (C$_1$-C$_6$)alkyl group, preferably a methyl group;
said process comprising the following steps:
a) the addition of an oxygen source into a solution of a compound of formula (II-1) in a water-miscible solvent, said compound of formula (II-1) having the following formula:

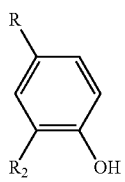

wherein R and R$_2$ are as defined above in formula (I-1),
b) the addition of a laccase in the solution obtained after step a); and
c) the possible recovering of the compound of formula (I-1) thus obtained.

The present invention also relates to a process for preparing a compound having the above-mentioned formula (I-2) wherein step a) is carried out with a compound having the following formula (II-2):

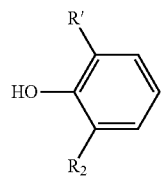

wherein R$_1$ and R$_2$ are as defined above in formula (I).
The present invention thus also relates to a process for preparing a compound having the following formula (I-2):

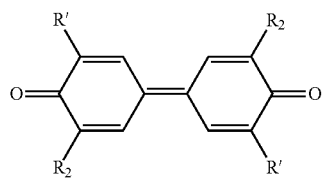

wherein:
R$_2$ is a (C$_1$-C$_6$)alkoxy group;
R' is a (C$_1$-C$_6$)alkoxy group;
said process comprising the following steps:
a) the addition of an oxygen source into a solution of a compound of formula (II-2) in a water-miscible solvent, said compound of formula (II-2) having the following formula:

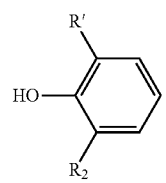

wherein R' and R$_2$ are as defined above in formula (I-2),
b) the addition of a laccase in the solution obtained after step a); and
c) the possible recovering of the compound of formula (I-2) thus obtained.

According to a preferred embodiment, the present invention relates to a process for preparing a compound having formula (I) (or formula (I-1) or (I-2)), comprising steps a) and b), as mentioned above, wherein the obtained compound is a precipitate.

According to such embodiment, the process according to the invention comprises a subsequent step for recovering the compound of formula (I) from the liquid reaction medium, said liquid reaction medium including the water-miscible solvent. For this recovering step, one may implement any method known by the skilled person for isolating a solid product from a liquid medium, such as in particular centrifugation or filtration.

According to a preferred embodiment, the method of the invention comprises, as step c), the recovering of the compound of formula (I) by the implementation of a filtration and/or centrifugation step.

Compounds of Formula (I)

The process of the invention is implemented to prepare compounds of formula (I) which could also be named 'dimers'.

In formula (I) as mentioned above, the link 'a' between the cores A and B is defined as a single (—) or a double (═) bond, depending on the definitions of the radicals present on these cores. As represented in this formula, when a is a single bond, the dotted line is absent and when a is a double bond, the dotted line represents a bond.

In a similar way, the dotted lines in the cores A and B correspond either to a ring of formula

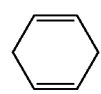

(when a is a double bond) or to a ring of formula

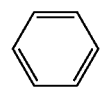

(when a is a single bond).

In formula (I), the $R_1$ group of core A and the $R_1$ group of core B are identical; the $R_2$ group of core A and the $R_2$ group of core B are identical; the $R_3$ group of core A and the $R_3$ group of core B are identical and the $R_4$ group of core A and the $R_4$ group of core B are identical.

According to an embodiment, in formula (I) or in formula (I-1), R is chosen from the group consisting of: —CHO, —CN, —COMe, —COOMe, —Me, and —CH$_2$—CH═CH$_2$.

According to an embodiment, in formula (I) or in formula (I-2), R' is methoxy.

According to an embodiment, in formula (I), (I-1), (I-2), (II-1) or (II-2), $R_2$ is a methoxy group.

According to an embodiment, in formula (II) or in formula (II-1), R is chosen from the group consisting of: —CHO, —CN, —COMe, —COOMe, —Me, and —CH$_2$—CH═CH$_2$.

According to an embodiment, in formula (II) or in formula (II-2), R' is methoxy.

The present invention also relates to the preparation of a compound having the above-mentioned formula (I-1) wherein $R_2$ is a methoxy group.

The present invention also relates to the preparation of a compound having the above-mentioned formula (I-2) wherein $R_2$ is a methoxy group.

More particularly, the process of the invention allows the preparation of one of the following compounds:

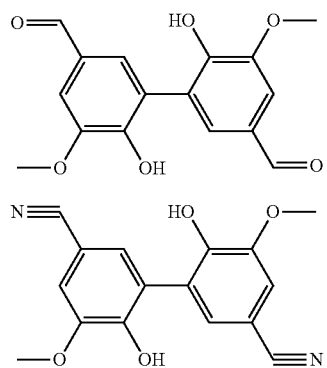

(1)

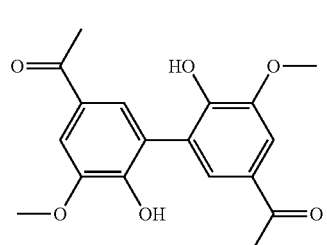

(2)

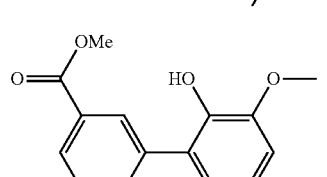

(3)

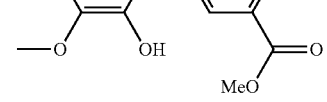

(4)

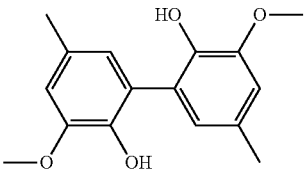

(5)

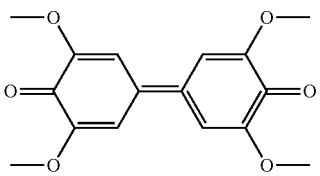

(6)

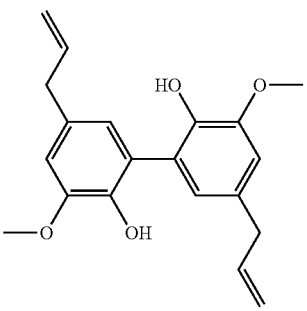

(7)

The process of the invention comprises two main steps a) and b) as described above.

Step a) consists in adding an oxygen source into a solution of a compound of formula (II) in a water-miscible solvent.

According to the invention, the solution of the compound of formula (II) in a water-miscible solvent may be prepared by adding said compound of formula (II) in said water-miscible solvent, and optionally adding a buffer solution, preferably a sodium acetate buffer.

According to an embodiment, the above-mentioned solution of the compound of formula (II) also comprises a buffer, the amount of said buffer being such that the pH of said solution is comprised between 4 and 7. According to a preferred embodiment, the buffer is sodium acetate.

In other words, the pH of the solution of the compound of formula (II) in the water-miscible solvent is preferably comprised between 4 and 7.

According to a preferred embodiment, the process of the invention is carried out at a pH comprised between 4 and 7. This pH range is appropriate as it corresponds to the pH range wherein the enzyme laccase is not altered.

Solvent

The solvent used for the process of the invention is suitable for enzymatic processes and is water-miscible.

According to an embodiment, the water-miscible solvent is chosen from the group consisting of: dioxane, DMSO, acetone, and mixtures thereof. Preferably, the water-miscible solvent is chosen from the group consisting of: DMSO, acetone, and mixtures thereof.

The preferred solvents according to the invention are chosen among the solvents in which the compound of formula (I) is able to form a precipitate.

Preferably, the water-miscible solvent is the acetone. According to an advantageous embodiment, step a) consists in adding an oxygen source in a solution of a compound of formula (II) in acetone, said solution being prepared by dissolving a compound of formula (II) in acetone.

According to a preferred embodiment, the amount of water-miscible solvent is comprised between 5% and 10% of volume in comparison with the total volume of the mixture formed by said solvent and the buffer solution. Most preferably, the percentage volume of the water-miscible solvent is 10% in comparison with the total volume of the mixture formed by said solvent and the buffer solution.

Oxygen Source

As mentioned above, the process of the invention comprises a step implementing an oxygen source.

In the present application, the term "oxygen source" refers to a reactant able to regenerate (re-oxide) the active sites of the laccase. The "oxygen" refers to dioxygene ($O_2$).

Preferably, the oxygen source is a gas comprising oxygen, such as air or pure oxygen.

As oxygen source, we may cite pure oxygen ($O_2$), which is added, by bubbling at atmospheric pressure or at a pressure of a few bars, into the reaction mixture comprising, at the start of the process, a compound of formula (II) and at least one water-miscible solvent, and if appropriate a buffer solution. This step is carried out to advantageously have the reaction medium saturated with dissolved oxygen.

Air or a mixture of any gas enriched in oxygen may be cited as oxygen source.

Step a) of the process of the invention consists in introducing said oxygen source into the reaction medium, said medium comprising a compound of formula (II) in solution in a water-miscible solvent. This introduction or addition may be carried out at a given moment or for a longer duration, preferably for a longer duration, the aim being to saturate the reaction medium in dissolved oxygen.

Alternatively, the oxygen source may be replaced with any oxidant able to regenerate (re-oxide) the active sites of the laccase used in the process.

According to an embodiment, the oxygen source is pure oxygen or air. Preferably, the oxygen source is pure oxygen.

According to an embodiment, this addition step is carried out for a sufficient time to saturate the solution in dissolved oxygen. Preferably, the addition of the oxygen source is carried out for 5 minutes.

According to a preferred embodiment, after step a), the solution of the compound of formula (II) in the water-miscible solvent is saturated in oxygen.

This saturated solution is then used for step b) which implements a laccase.

Laccase

Laccase (EC 1.10.3.2) is a very well-known class of oxidative enzyme studied since 1883. These glycoproteins which belong to the blue copper family of oxidase are found in several plants and fungus and are involved in lignification and delignification.

Laccases generate radical intermediates on phenolic compounds which can undergo self-coupling reactions. Generally, due to the delocalization of the radical, this reaction leads to different binding, and so a low selectivity of the synthesized compound.

The laccases which may be used in the process of the invention are found in plants, fungi and microorganisms.

Laccases from fungi include in particular laccases of genus *Aspergillus, Neurospora* (for example *Crassa Neurospora*), *Podospora, Botrytis, Collybia, Fomes, Lentinus, Pleurotus, Trametes* (for example *Trametes villosa* et *Trametes versicolor*), *Rhizoctonia* (for example *Rhizoctonia solani*), *Coprinus* (for example *Coprinus cinereus, Coprinus comatus, Coprinus friesii* et *Coprinus plicatilis*), *Psathyrella* (for example *Psathyrella condelleana*), *Panaeolus* (for example *Panaeolus papilionaceus*), *Myceliophthora* (for example *Myceliophthora thermophila*), *Schytalidium* (for example *Schytalidium thermophilum*), *Polyporus* (for example *Polyporus pinsitus*), *Phlebia* (for example *Radiata phlebia*), *Pycnoporus* (for example *Pycnoporus cinnabarinus*) or *Coriolus* (for example *Coriolus hirsutus*).

Laccases from bacteria are for example found in *Bacillus*.

Preferably, the laccase used in the invention is laccase from *Trametes versicolor*, marketed by Sigma Aldrich.

According to an embodiment, the amount of laccase for one gram of compound of formula (II) is from 3 U to 65 U. According to the present invention, U refers to the catalytic unit, one U being defined as the amount of the enzyme that formed 1 µmol of ABTS radical cation per minute.

In the present invention, the reference substrate is ABTS (2,2'-azino-bis(3-ethylbenzothiazoline-6-sulphonic acid).

Preferably, the amount of laccase is 13 U for 1 gram of compound of formula (II).

According to an embodiment, the amount of laccase for one gram of compound of formula (II) is from 1.5 mg to 75 mg, preferably from 3 mg to 15 mg.

As mentioned above, step b) consists in adding a laccase into the solution obtained after step a), said solution being also named 'solution of compound of formula (II) in a water-miscible solvent saturated in oxygen' or 'saturated solution' or 'saturated solution of compound of formula (II)'.

Once the laccase added, the reaction medium comprising the laccase and the saturated solution of compound of formula (II), may be stirred at a temperature comprised between 20° C. and 60° C., and preferably at room temperature.

According to an embodiment, this stirring step is carried out for at least one minute to several days, in particular for 5 minutes to 72 hours, and preferably for 24 hours.

During the stirring, the enzymatic reactions are carried out and allow the formation of the compound(s) of formula (I) as mentioned above.

According to an advantageous embodiment, the process of the invention (in particular steps a) and b)) is carried out under pressure. According to an advantageous embodiment, the process is carried out at atmospheric pressure.

According to an embodiment, the process of the invention comprises a subsequent step which consists in filtering the solution obtained after step b), washing it with water and then drying under vacuum in order to recover the precipitate. As the obtained product is in a solid form, it can be recovered by centrifugation and purified by recrystallization.

According to an embodiment, when the process comprises a step of filtering the solution obtained after step b) as mentioned above, the filtrate may be isolated and recovered. This filtrate is a liquid solution comprising laccase which could be recycled and used in the process of the invention.

Therefore, according to the invention, the laccase used in step b) may be used as pure laccase or as a solution recovered from the process of the invention.

The present invention also relates to the transformation of the dimers of formula (I-1) and (I-2) as mentioned above.

The present invention also relates to a process for the preparation of a compound having the following formula (III):

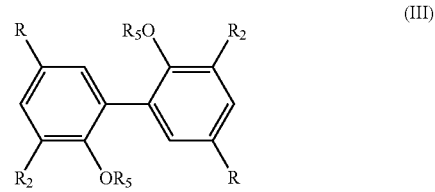

R and $R_2$ being as defined in formula (I), and
$R_5$ being a ($C_1$-$C_6$)alkyl group, preferably methyl, said process comprising the steps of:
preparing a compound of formula (I-1) using the process as mentioned above, said compound of formula (I-1) being thus prepared from a compound of formula (II-1) as defined above,
alkylating the compound of formula (I-1) with a compound $R_5X$, X being a halogen atom, preferably I,
and the possible recovering of the compound of formula (III).

According to an embodiment, in formula (III), R is —CHO, —$CH_2$—CH=$CH_2$ or COOR$_a$, R$_a$ being as defined above in formula (I), and being preferably methyl.

According to an embodiment, in formula (III), $R_2$ is a methoxy group.

This process consists thus in alkylating a compound of formula (I-1) as obtained according to the process as described above comprising steps a) and b).

The process of preparation of the compounds of formula (III) corresponds to the process as mentioned above for preparing a compound of formula (I-1) which comprises a subsequent alkylation step of said compound of formula (I-1).

Preferred compounds of formula (III) have the following formula (III-1):

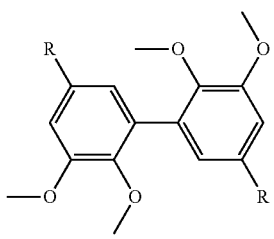

(III-1)

R being as defined in formula (I), and most preferably are chosen from the following compounds:

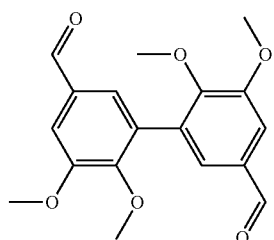

(9)

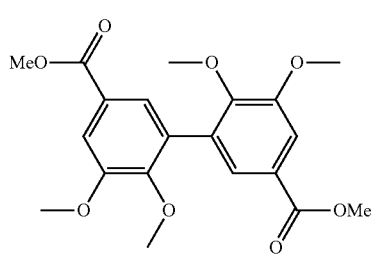

(11)

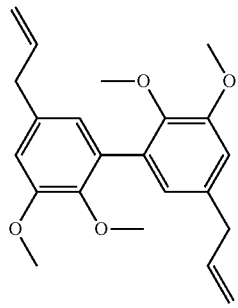

(18)

Preferably, the alkylation step as mentioned above is carried out with a compound $R_5I$. According to a preferred embodiment, this alkylation step is carried out in dimethylformamide (DMF) with $K_2CO_3$ at 80° C. for 20 hours, such alkylation conditions being well known from the skilled person.

The present invention also relates to a process for the preparation of a compound having the following formula (IV):

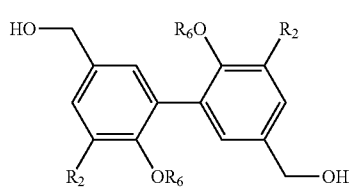

(IV)

$R_2$ being as defined above in formula (I), and
$R_6$ being H or a ($C_1$-$C_6$)alkyl group,
said process comprising the steps of:
preparing a compound of formula (I-1) with R being CHO, using the process as mentioned above,
reacting the compound of formula (I-1) with a hydrogenation agent, such as $NaBH_4$, in order to obtain a compound of formula (IV) wherein $R_6$=H,
and, if necessary, alkylating the compound of formula (IV) wherein $R_6$=H with a compound $R_5X$, X being a halogen, preferably I, and $R_5$ being a ($C_1$-$C_6$) alkyl group, in order to obtain a compound of formula (IV) wherein $R_6$=($C_1$-$C_6$) alkyl,
and the possible recovering of the compound of formula (IV).

The process of preparation of the compounds of formula (IV) corresponds to the process as mentioned above for preparing a compound of formula (I-1) with R=CHO which comprises a subsequent reaction of hydrogenating the aldehyde moiety (into a —$CH_2OH$ group).

According to an embodiment, in formula (IV), $R_2$ is a methoxy group.

Preferably, the hydrogenation step as mentioned above is carried out with $NaBH_4$ as hydrogenation agent or any other well-known hydrogenation agent. According to a preferred embodiment, this hydrogenation step is carried out in methanol.

Preferred compounds of formula (IV) have the following formula (IV-1):

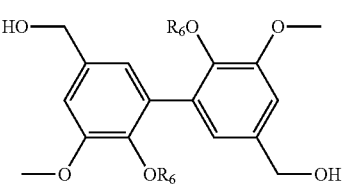

(IV-1)

$R_6$ being as defined above, and being preferably H or methyl, and most preferably are chosen from the following compounds:

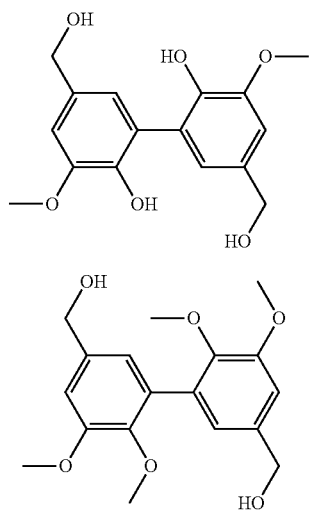

(8)

(10)

The present invention also relates to a process for the preparation of a compound having the following formula (V):

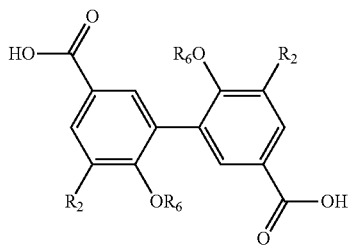

(V)

$R_2$ being as defined in formula (I), and
$R_6$ being H or a $(C_1$-$C_6)$alkyl group,
said process comprising the steps of:
preparing a compound of formula (I-1) with R being $COOR_a$, using the process as mentioned above,
reacting the compound of formula (I-1) with methanol in the presence of a base, such as KOH or any other source of hydroxide, in order to obtain a compound of formula (V) wherein $R_6$=H,
and, if necessary, alkylating the compound of formula (V) wherein $R_6$=H with a compound $R_5X$, X being a halogen, preferably I, and $R_5$ being a $(C_1$-$C_6)$ alkyl group, in order to obtain a compound of formula (V) wherein $R_6$=$(C_1$-$C_6)$ alkyl,
and the possible recovering of the compound of formula (V).

The process of preparation of the compounds of formula (V) corresponds to the process as mentioned above for preparing a compound of formula (I-1) with R=$COOR_a$ which comprises a subsequent reaction of reacting the compound of formula (I-1) with methanol in the presence of a base (which consists in transforming the $COOR_a$ group into a COOH group).

According to an embodiment, in formula (V), $R_2$ is a methoxy group.

Preferably, the subsequent step as mentioned above is carried out with methanol and KOH, in particular for 10 hours at 40° C. According to a preferred embodiment, this hydrogenation step is carried out in methanol.

Preferred compounds of formula (V) have the following formula (V-1):

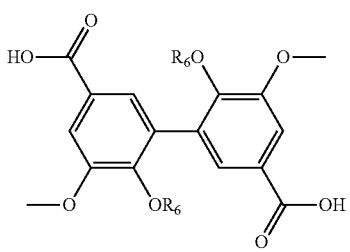

(V-1)

$R_6$ being as defined above, and being preferably H or methyl, and most preferably are chosen from the following compounds:

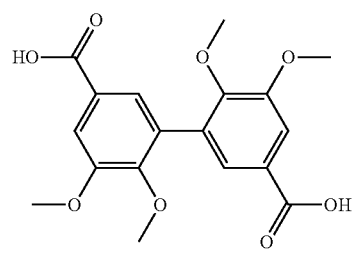

(12)

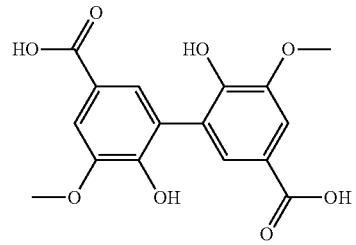

(13)

The present invention also relates to a process for the preparation of a compound having the following formula (VI):

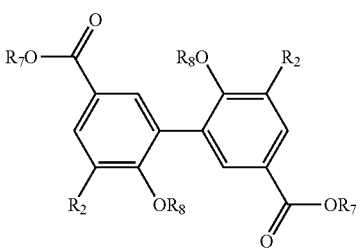

(VI)

$R_2$ being as defined in formula (I),
$R_7$ being a $(C_2$-$C_{10})$alkenyl group, and
$R_8$ being a $(C_1$-$C_6)$alkyl group, said process comprising the steps of:
preparing a compound of formula (V) with $R_6$ being a $(C_1-C_6)$alkyl group, using the process as mentioned above,
reacting the compound of formula (V) with an alcohol $R_7OH$ in the presence of a catalyst, such as PTSA/DMAP, and of N,N'-diisopropyl carbodiimide, especially in stoichiometric quantities, in order to obtain a compound of formula (VI),
and the possible recovering of the compound of formula (VI).

The process of preparation of the compounds of formula (VI) corresponds to the process as mentioned above for preparing a compound of formula (V) with $R_6=(C_1-C_6)$ alkyl group which comprises a subsequent reaction of reacting the compound of formula (V) with an alcohol $R_7OH$ (which consists in transforming the COOH group into a $COOR_7$ group).

According to an embodiment, in formula (VI), $R_2$ is a methoxy group.

According to an embodiment, in formula (VI), $R_8$ is a methyl group.

Preferably, the step as mentioned above of reacting the compound of formula (V) with the alcohol $R_7OH$ is carried out with a PTSA/DMAP catalyst, in particular at room temperature, for 72 hours. According to a preferred embodiment, this step is carried out in dichloromethane.

Preferred compounds of formula (VI) have the following formula (VI-1):

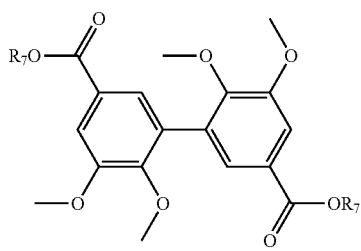

$R_7$ being as defined above,

A most preferred compound of formula (VI) is the following compound:

(14)

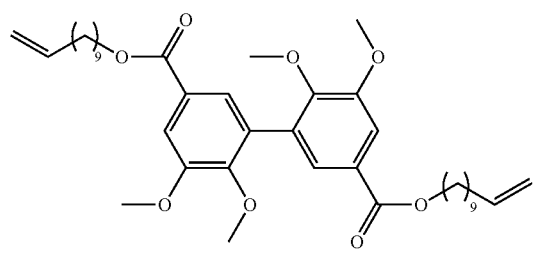

The present invention also relates to a process for the preparation of a compound having the following formula (VII):

(VII)

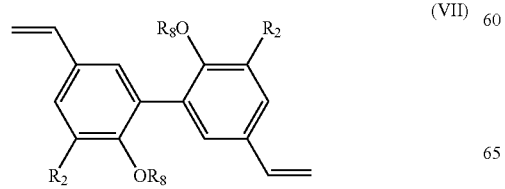

$R_2$ being as defined in formula (I), and
$R_8$ being a $(C_1-C_6)$alkyl group, said process comprising the steps of:
preparing a compound of formula (I-1) with R being CHO, using the process as mentioned above,
alkylating the compound of formula (I-1) with a compound $R_8X$, X being a halogen, preferably I, for obtaining a compound having the following formula (III-1):

(III-1)

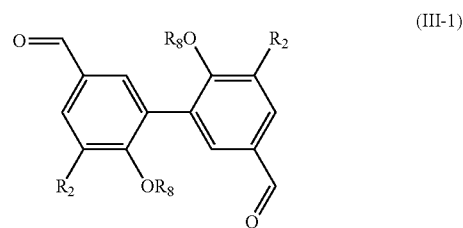

$R_2$ and $R_8$ being as defined above in formula (VIII), reacting the compound of formula (III-1) with a Wittig reagent, in order to obtain a compound having the formula (VII), and the possible recovering of the compound of formula (VII).

The term 'Wittig reagent' is a term well-known in the art which refers to a triphenyl phosphonium ylide.

Alternatively, the compound of formula (VII) may be prepared from a compound of formula (III-1) by implementing a Wittig-Horner reaction instead of the Wittig reaction as mentioned above.

The process of preparation of the compounds of formula (VII) corresponds to the process as mentioned above for preparing a compound of formula (I-1) with R=CHO which comprises a subsequent step of alkylating the compound of formula (I-1) as well as a subsequent step of reacting the alkylated compound of formula (III-1) with a Wittig reactant (these steps consist in transforming the CHO group into a $-CH=CH_2$ group).

According to an embodiment, in formula (VII), $R_2$ is a methoxy group.

According to an embodiment, in formula (VII), $R_8$ is a methyl group.

Preferably, the step of reacting the compound of formula (III-1) with a Wittig reactant as mentioned above is carried out in THF, in particular for 24 hours at room temperature. According to a preferred embodiment, this step also comprises the use of potassium tert-butoxide.

A preferred compound of formula (VII) has the following formula (15):

(15)

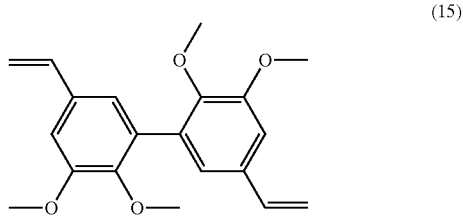 [SMILES: C=Cc1cc(OC)c(OC)c(-c2cc(C=C)cc(OC)c2OC)c1]

The present invention also relates to a process for the preparation of a compound having the following formula (VIII):

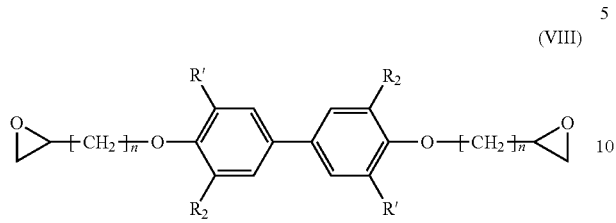
(VIII)

R' and R$_2$ being as defined in formula (I-2), and n being an integer varying from 1 to 6, said process comprising the steps of:

preparing a compound of formula (I-2), using the process as mentioned above, reacting the compound of formula (I-2) with a hydrogenation agent such as NaBH$_4$, in order to obtain a compound having the following formula (VIII-1):

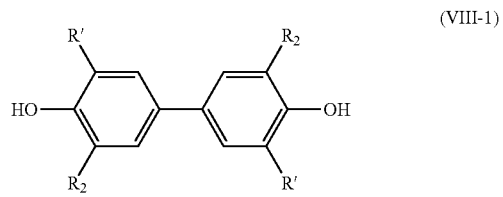
(VIII-1)

R' and R$_2$ being as defined in formula (I-2), reacting the compound of formula (VIII-1) in the presence of a base, such as KOH, with a compound having the following formula (IX):

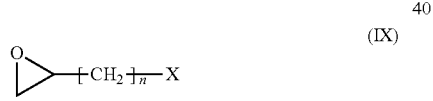
(IX)

n being as defined above, and X being a halogen atom, such as Cl, in order to obtain a compound of formula (VIII), and the possible recovering of the compound formula (VIII).

The process of preparation of the compounds of formula (VIII) corresponds to the process as mentioned above for preparing a compound of formula (I-2) which comprises a subsequent step of hydrogenating the compound of formula (I-2) as well as a subsequent step of reacting the compound of formula (VIII-1) with a compound of formula (IX)(in order to obtain bisepoxide compounds).

According to an embodiment, in formula (VIII), R$_2$ is a methoxy group.

According to an embodiment, in formula (VIII), R' is a methoxy group.

Preferably, the step of hydrogenating the compound of formula (I-2) is carried out with NaBH$_4$ in ethanol. Preferably, the step of reacting the compound of formula (VIII-1) with a compound of formula (IX) comprises the addition of potassium hydroxide and tetrabutylammonium bromide.

A preferred compound of formula (VIII-1) has the following formula (16):

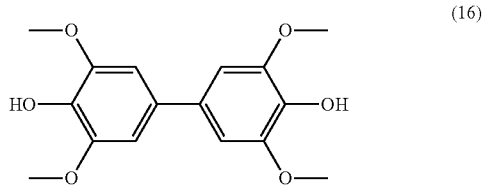 [SMILES: COc1cc(-c2cc(OC)c(O)c(OC)c2)cc(OC)c1O]
(16)

A preferred compound of formula (VIII) has the following formula (17):

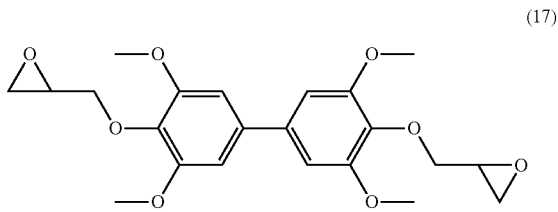 [SMILES: COc1cc(-c2cc(OC)c(OCC3CO3)c(OC)c2)cc(OC)c1OCC1CO1]
(17)

The present invention also relates to a process for the preparation of a compound having the following formula (X):

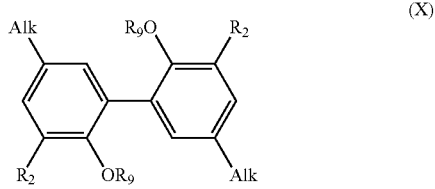
(X)

Alk being a (C$_1$-C$_6$)alkyl group,

R$_2$ being as defined in formula (I-1), and

R$_9$ being a (C$_2$-C$_{10}$)alkenyl group, said process comprising the steps of:

preparing a compound of formula (I-1) with R being a (C$_1$-C$_6$)alkyl group, using the process as mentioned above, reacting the compound of formula (I-1) with a compound R$_7$X, X being a halogen, preferably Br, in the presence of K$_2$CO$_3$ in a solvent such as DMF, and the possible recovering of the compound of formula (X).

The process of preparation of the compounds of formula (X) corresponds to the process as mentioned above for preparing a compound of formula (I-1) with R=(C$_1$-C$_6$) alkyl group, which comprises a subsequent step of reacting the compound of formula (I-1) with a compound R$_7$X.

According to an embodiment, in formula (X), R$_2$ is a methoxy group.

According to an embodiment, in formula (X), Alk is a methyl group.

Preferably, the step of reacting the compound of formula (I-1) with the compound R$_7$X is carried out in DMF in the presence of potassium carbonate. Preferably, this step is carried out for 20 hours at 80° C.

A preferred compound of formula (X) has the following formula (19):

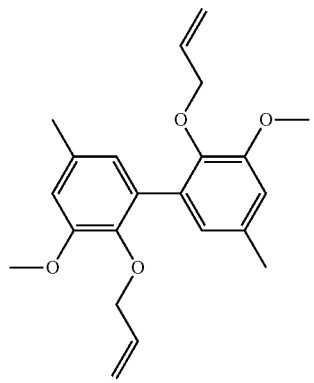

(19)

The present invention also relates to a compound having one of the above formulae (2), (14), (15), and (19).

As used herein, the term "$(C_x\text{-}C_y)$alkyl" means a saturated aliphatic hydrocarbon group, which may be straight or branched, having x to y carbon atoms in the chain. Preferred alkyl groups have 1 to about 12, preferably 1 to 10, and more preferably 1 to 6, carbon atoms in the chain. The following alkyl groups may be cited as example: methyl, ethyl, propyl, butyl, pentyl, hexyl, heptyl, octyl, nonyl, decyl, dodecyl.

As used herein, the term "$(C_x\text{-}C_y)$alkylene" (or "alkylidene") refers to a divalent saturated aliphatic hydrocarbon radical, comprising from x to y carbon atoms, having preferably from 1 to 20, in particular 1 to 12 carbon atoms, and more preferably 2 to 10 carbon atoms. When said radical is linear, it may be represented by the formula $(CH_2)_m$ wherein m is an integer varying from 1 to 12, and preferably from 2 to 10. The following alkylene may be cited as example: methylene, ethylene, propylene, butylene, pentylene, hexylene, heptylene, octylene, nonylene, decylene, dodecylene.

As used herein, the term "$(C_x\text{-}C_y)$alkenyl" means an aliphatic hydrocarbon group containing a carbon-carbon double bond and which may be straight or branched having x to y carbon atoms in the chain. Preferred alkenyl groups have 2 to 12 carbon atoms in the chain; and more preferably about 2 to 10 or 2 to 6 carbon atoms in the chain. Exemplary alkenyl groups include for example ethenyl, propenyl, n-butenyl, i-butenyl, 3-methylbut-2-enyl, n-pentenyl, heptenyl, octenyl, nonenyl, decenyl.

As used herein, the term "alkenylene" means a hydrocarbon radical having at least one carbon-carbon double bond (straight chain or branched) wherein a hydrogen atom is removed from each of the terminal carbons such as ethenylene, propenylene, and the like.

As used herein, the term "alkoxy" means an alkyl-O— group wherein the alkyl group is as herein described. Exemplary alkoxy groups include methoxy, ethoxy, n-propoxy, i-propoxy, n-butoxy and heptoxy.

The invention is described in the foregoing by way of non-limiting examples.

EXAMPLES

Preparation of Compounds of Formula (I)

Vanillin, 2-methoxy-4-methylphenol and 2,6-dimethoxyphenol were supplied by Alfa Aesar; Eugenol was purchased from Sigma Aldrich and Acetovanillon was bought from Acros organic.

Enzymatic Dimerization: General Procedure

A solution of 1.5 g of compound of formula (II) in 20 mL of acetone was added to 180 mL of NaOAc buffer (0.1 M, pH 5.0). The solution was saturated in $O_2$ for 5 min. Laccase from Trametes versicolor (20 U, 12.4 mg) was added and the reaction was stirred at room temperature for 24 hours. The precipitate was filtered, washed with water and dried under vacuum (at 100° C. overnight). This procedure is was adapted on 15 g in the case of vanillin.

Kinetic Investigation

The enzymatic dimerization general procedure is followed using vanillin and 0.1 mL of dioxane, used as reference is added in the solution. 0.4 mL of solution is sampled regularly, filtered and diluted in deuteriated acetone. The samples are analyzed by NMR. The vanillin conversion is extracted from the ratio of CHO peak integration at 9.81 ppm and the dioxane peak integration at 3.63 ppm.

Observations

After introduction of the laccase, the uncolored solution turned to yellow, revealing the creation of radicals. After few minutes, a brown precipitate appeared.

Example 1: Preparation of Compound (1)

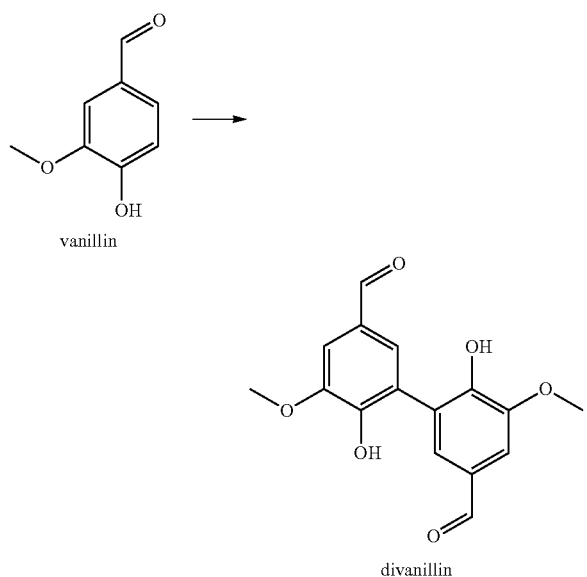

A solution of 1.5 g of vanillin in 20 mL of acetone was added to 180 mL of NaOAc buffer (0.1 M, pH 5.0). The solution was saturated in $O_2$ for 5 min. Laccase from Trametes versicolor (20 U, 12.4 mg) was added and the reaction was stirred at room temperature for 24 hours. The precipitate was filtered, washed with water and dried under vacuum (at 100° C. overnight).

Yield: 96%

Analyses:

Mass: 302.1 (100%), 303.1 (18%), 304.1 (2%);

$^1$H NMR: δ 9.85 (s, CHO), 7.50 (s, 2H Ar), 4.00 (s, OCH$_3$);

$^{13}$C NMR: δ 191.04 (CHO), 150.70 (Ar—C), 147.95 (Ar—C), 128.30 (Ar—C), 127.69 (Ar—C), 124.52 (Ar—C), 109.10 (Ar—C), 55.88 (OCH$_3$).

Example 2: Preparation of Compound (2)

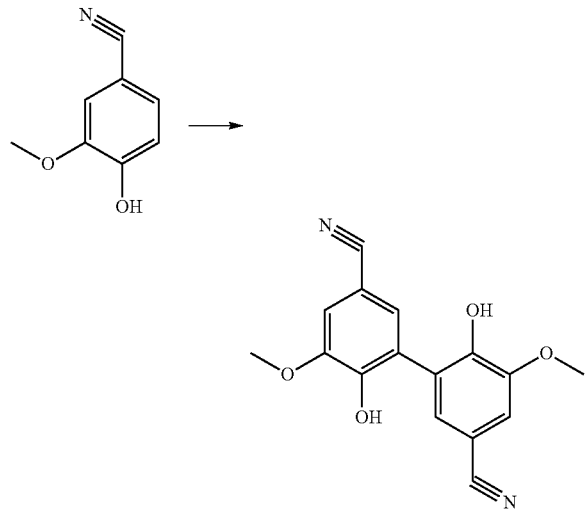

Compound (2) is prepared from 4-hydroxy-3-methoxy-benzonitrile with a yield of 95%.

4-Hydroxy-3-methoxybenzonitrile synthesis 750 mg (5 mmol) of vanillin were dissolved in 15 mL of acetic acid. 520 mg of $NH_2OH \cdot HCl$ (7.5 mmol) are added and the mixture was stirred and warmed at 110° C. for 2 h. The reaction was stopped by adding $H_2O$, the organic product extracted using $CH_2Cl_2$, dried and purified by flash chromatography (Ethyl acetate/cyclohexane 3/7).

Dimerization

A solution of 1.5 g of compound of 4-hydroxy-3-methoxybenzonitrile in 20 mL of acetone was added to 180 mL of NaOAc buffer (0.1 M, pH 5.0). The solution was saturated in $O_2$ for 5 min. Laccase from Trametes versicolor (20 U, 12.4 mg) was added and the reaction was stirred at room temperature for 24 hours. The precipitate was filtered, washed with water and dried under vacuum (at 100° C. overnight).

Analyses:

Mass: 296.1 (100%), 297.1 (18%), 298.1 (2%);

$^1$H NMR: δ 9.91 (s, 2H, HO), 7.57 (s, 2H, Ar), 7.42 (s, 2H, Ar), 3.93 (s, 6H, $OCH_3$);

$^{13}$C NMR: δ 148.63 (Ar—C), 147.85 (Ar—C), 128.05 (Ar—C), 124.56 (Ar—C), 119.45 (Ar—C), 114.03 (Ar—C), 100.30 (CN), 56.15 ($OCH_3$).

Example 3: Preparation of Compound (3)

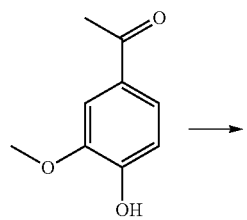

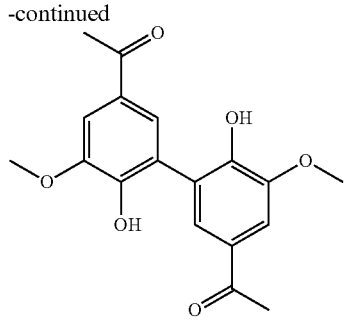

A solution of 1.5 g of compound of acetovanillone in 20 mL of acetone was added to 180 mL of NaOAc buffer (0.1 M, pH 5.0). The solution was saturated in $O_2$ for 5 min. Laccase from Trametes versicolor (20 U, 12.4 mg) was added and the reaction was stirred at room temperature for 24 hours. The precipitate was filtered, washed with water and dried under vacuum (at 100° C. overnight).

Compound (3) is prepared from acetovanillone with a yield of 92%.

Analyses:

Mass: 330.1 (100%), 331.1 (18%), 332.2 (2%);

$^1$H NMR: δ 7.49 (s, 4H, Ar), 3.93 (s, 6H, $OCH_3$), 2.56 (s, 6H, C=$OCH_3$);

$^{13}$C NMR: δ 196.07 (OCH), 149.22 (Ar—C), 147.06 (Ar—C), 127.81 (Ar—C), 124.23 (Ar—C), 124.04 (Ar—C), 109.03 (Ar—C), 55.76 ($OCH_3$), 26.25 ($CH_3$).

Example 4: Preparation of Compound (4)

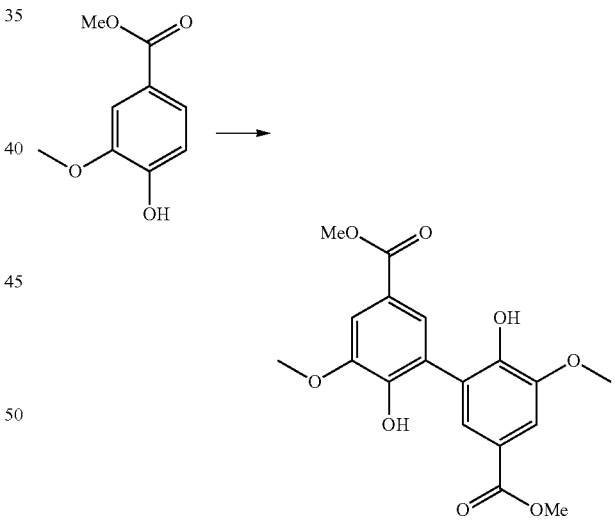

A solution of 1.5 g of compound of methylvanillate in 20 mL of acetone was added to 180 mL of NaOAc buffer (0.1 M, pH 5.0). The solution was saturated in $O_2$ for 5 min. Laccase from Trametes versicolor (20 U, 12.4 mg) was added and the reaction was stirred at room temperature for 24 hours. The precipitate was filtered, washed with water and dried under vacuum (at 100° C. overnight).

Compound (4) is prepared from methylvanillate with a yield of 90%.

Methyl Vanillate Synthesis 15 g of vanillic acid (0.09 mol) were dissolved in 75 mL of methanol. 2.1 mL of sulfuric acid were added and the mixture is stirred and warm to reflux for 8 h. After evaporation of methanol, the solid is dissolved in 60 mL of ethylacetate, washed with 30 mL of NaHCO$_3$ solution, water (2 times) and brine (1 time). The organic phase is evaporated under reduced pressure.

Analyses:

Mass: 362.1 (100%), 363.1 (20%), 364.1 (2%);

$^1$H NMR: δ 9.60 (s, 2H, HO), 7.46 (s, 4H, Ar), 3.90 (s, 6H, OCH$_3$), 3.80 (s, 6H, OCH$_3$ ester);

$^{13}$C NMR: δ 166.04 (OCH$_3$ester), 148.60 (Ar—C), 147.27 (Ar—C), 125.25 (Ar—C), 123.93 (Ar—C), 119.21 (Ar—C), 110.89 (Ar—C), 55.97 (OCH$_3$), 51.75 (OCH$_3$ ester).

Example 5: Preparation of Compound (5)

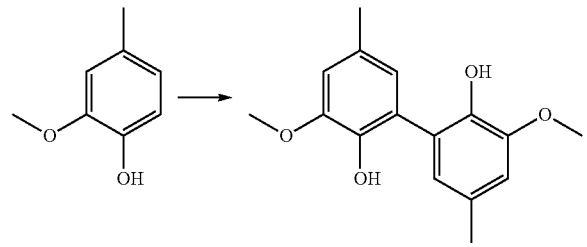

A solution of 1.5 g of compound of 2-methoxy-4-methylphenol in 20 mL of acetone was added to 180 mL of NaOAc buffer (0.1 M, pH 5.0). The solution was saturated in O$_2$ for 5 min. Laccase from Trametes versicolor (20 U, 12.4 mg) was added and the reaction was stirred at room temperature for 24 hours. The precipitate was filtered, washed with water and dried under vacuum (at 100° C. overnight).

Compound (5) is prepared from 2-methoxy-4-methylphenol with a yield of 92%.

Analyses:

Mass: 274.1 (100%), 275.1 (18%), 276.1 (2%);

$^1$H NMR: δ 6.73 (s, 2H, Ar), 6.53 (s, 2H, Ar), 3.79 (s, 6H, OCH$_3$), 2.23 (s, 6H, CH$_3$);

$^{13}$C NMR: δ 147.52 (Ar—C), 140.99 (Ar—C), 126.92 (Ar—C), 125.68 (Ar—C), 123.04 (Ar—C), 111.61 (Ar—C), 55.85 (OCH$_3$), 20.65 (CH$_3$).

Example 6: Preparation of Compound (6)

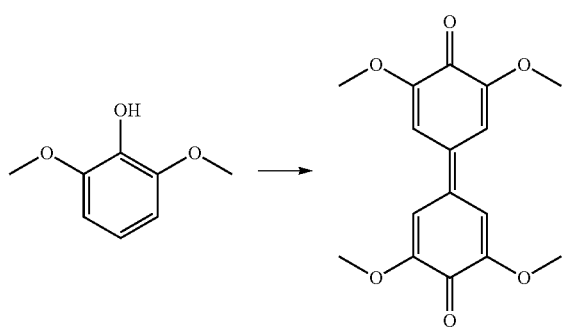

A solution of 1.5 g of compound of 2,6-dimethoxy-phenol in 20 mL of acetone was added to 180 mL of NaOAc buffer (0.1 M, pH 5.0). The solution was saturated in O$_2$ for 5 min. Laccase from Trametes versicolor (20 U, 12.4 mg) was added and the reaction was stirred at room temperature for 24 hours. The precipitate was filtered, washed with water and dried under vacuum (at 100° C. overnight).

Compound (6) is prepared from 2,6-dimethoxy-phenol with a yield of 90%.

Analyses:

Mass: 304.1 (100%), 305.1 (18%), 318.1 (2%);

$^1$H NMR: δ 8.32 (s, 2H, HO), 6.82 (s, 4H, Ar), 3.84 (s, 12H, OCH$_3$).

Example 7: Preparation of Compound (7)

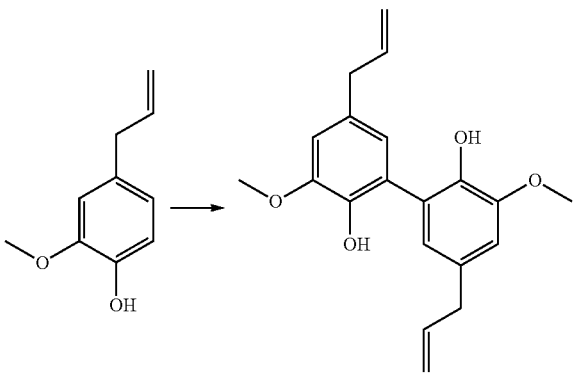

A solution of 1.5 g of compound of eugenol in 20 mL of acetone was added to 180 mL of NaOAc buffer (0.1 M, pH 5.0). The solution was saturated in O$_2$ for 5 min. Laccase from Trametes versicolor (20 U, 12.4 mg) was added and the reaction was stirred at room temperature for 24 hours. The precipitate was filtered, washed with water and dried under vacuum (at 100° C. overnight).

Compound (7) is prepared from eugenol with a yield of 87%.

Analyses:

Mass: 327.2 (100%), 326.2 (20%), 328.3 (10%);

$^1$H NMR: δ 6.74 (s, 2H Ar), 6.52 (s, 2H Ar), 5.94 (q, 2H CH—CH$_2$), 5.03 (d, 4H CH—CH$_2$), 3.79 (s, OCH$_3$), 3.27 (d, 2H CH$_2$);

$^{13}$C NMR: δ 147.80 (Ar—C), 141.62 (Ar—C), 138.38 (CH—CH$_2$), 129.57 (Ar—C), 125.67 (Ar—C), 122.62 (Ar—C), 115.28 (Ar—C), 105.56 (CH—CH$_2$), 55.64 (OCH$_3$), 39.19 (CH$_2$).

The above results show several advantages of the process of the invention:

It is a green reaction.

Indeed the divanillin formation occurs at room temperature, under oxygen which could be replaced by air. The solvent used shows a low toxicity. To ensure the solubility of vanillin into the reaction medium, the compound was totally dissolved into acetone (10%) before adding the acetate buffer (90%).

The product extraction is easy and the purity is high (95%). Indeed, the solvent conditions allowed the reactant solubility while the so formed product precipitated. The precipitate was filtered off, washed with water and analyzed by mass spectroscopy, NMR, and HPLC.

A low quantity of enzyme is needed and can be reused. The experiments of the above examples were performed using 20 U of laccase. This amount is the minimal amount necessary to reach more than 85% conversion after 24 h. With 5 U or 10 U, 50% conversion is reached after 24 h.

The experiments are as follows:

5U:
A solution of 1.5 g of compound of vanillin in 25 mL of acetone was added to 225 mL of NaOAc buffer (0.1 M, pH 5.0). The solution was saturated in O₂ for 5 min. Laccase from Trametes versicolor (5 U, 3.1 mg) was added and the reaction was stirred at room temperature for 24 hours. The precipitate was filtered, washed with water and dried under vacuum (at 100° C. overnight) and weighted.

10U:
A solution of 1.5 g of compound of vanillin in 25 mL of acetone was added to 225 mL of NaOAc buffer (0.1 M, pH 5.0). The solution was saturated in O₂ for 5 min. Laccase from Trametes versicolor (10 U, 6.2 mg) was added and the reaction was stirred at room temperature for 24 hours. The precipitate was filtered, washed with water and dried under vacuum (at 100° C. overnight) and weighted.

20U:
A solution of 1.5 g of compound of vanillin in 25 mL of acetone was added to 225 mL of NaOAc buffer (0.1 M, pH 5.0). The solution was saturated in O₂ for 5 min. Laccase from Trametes versicolor (20 U, 12.4 mg) was added and the reaction was stirred at room temperature for 24 hours. The precipitate was filtered, washed with water and dried under vacuum (at 100° C. overnight) and weighted.

50U:
A solution of 1.5 g of compound of vanillin in 25 mL of acetone was added to 225 mL of NaOAc buffer (0.1 M, pH 5.0). The solution was saturated in O₂ for 5 min. Laccase from Trametes versicolor (50 U, 31 mg) was added and the reaction was stirred at room temperature for 24 hours. The precipitate was filtered, washed with water and dried under vacuum (at 100° C. overnight) and weighted.

100U:
A solution of 1.5 g of compound of vanillin in 25 mL of acetone was added to 225 mL of NaOAc buffer (0.1 M, pH 5.0). The solution was saturated in O₂ for 5 min. Laccase from Trametes versicolor (100 U, 62 mg) was added and the reaction was stirred at room temperature for 24 hours. The precipitate was filtered, washed with water and dried under vacuum (at 100° C. overnight) and weighted.

The results of the above experiments are as follows:

| Laccase units | Yield (%) |
|---|---|
| 100 | 85 |
| 50 | 85 |
| 20 | 87 |
| 10 | 54 |
| 5 | 56 |

Kinetic studies were realized and showed a good conversion, over 85% (not over due to NMR sensitivity) and a very high yield, over 90% after 24 h.

The fact the divanillin precipitates while vanillin is still soluble allows the solution to be reused for a new reaction after filtration of divanillin.

Refill Procedure

After 24 h of reaction, the precipitate was filtered and vanillin was added in the solution which was saturated in oxygen again. This experiment was repeated 8 times and the yield was still as high as 95%.

The following experiment was carried out:

A solution of 1.5 g of compound of vanillin in 25 mL of acetone was added to 225 mL of NaOAc buffer (0.1 M, pH 5.0). The solution was saturated in O₂ for 5 min. Laccase from *Trametes versicolor* (50 U, 31 mg) was added and the reaction was stirred at room temperature for 24 hours. The precipitate was filtered, washed with water and dried under vacuum (at 100° C. overnight) and weighted. The filtrate was kept. 1.5 g of vanillin was added in the solution which was saturated in oxygen again. The reaction was stirred at room temperature for 24 hours. The precipitate was filtered, washed with water and dried under vacuum (at 100° C. overnight) and weighted. This experiment was repeated 8 times.

| | Yield (%) |
|---|---|
| 1st reaction | 84 |
| Refill 1 | 95 |
| Refill 2 | 84 |
| Refill 3 | 93 |
| Refill 4 | 80 |
| Refill 5 | 85 |
| Refill 6 | 95 |
| Refill 7 | 92 |
| Refill 8 | 96 |

Chemical Modifications of Compounds of Formula (i)

Sodium borohydride, potassium hydroxide, triphenylphosphine, allyl bromide were supplied by Alfa Aesar.

Sodium acetate, acetic acid, laccase, hydroxylamine hydrochloride, sulfuric acid, iodomethane, 4-toluenesulfonic acid and N,N'-diisopropylcarbodiimide were purchased from Sigma Aldrich.

4-dimethylaminopyridine was bought from Acros organic, potassium carbonate was supplied by Prolabo, potassium tert-butoxide was purchased at ABCR and epichlorohydrine was bought at TCI.

Example 8: Preparation of Compound (8)

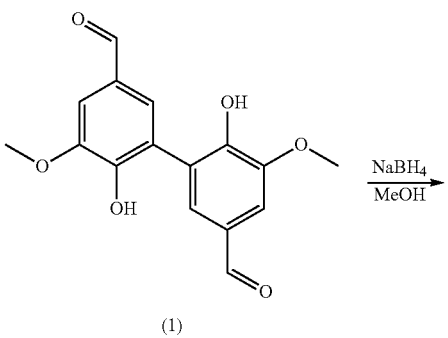

(1)

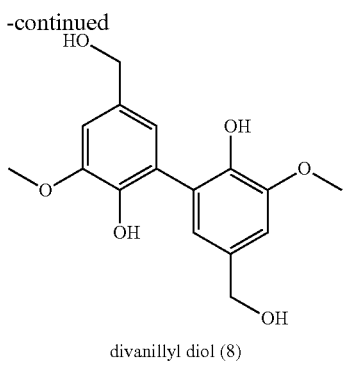

divanillyl diol (8)

20 mmol of divanillin (≈6 g) were dissolved in 100 mL of ethanol. The flask was put in an ice bath and 3.6 g of sodium borohydride (100 mmol) were added slowly. Then the mixture was stirred at room temperature for 30 min. 45 mL of water were added to stop the reaction and the solution is acidified with HCl to pH 7 and warmed for 5 min at 50° C. The solvent was evaporated; the resulting solid was solubilized in dichloromethane and washed 3 times with water. Yield: 80%.

Analyses:
$^1$H NMR: δ 8.25 (s, OH phenol), 6.9 (s, 2H Ar), 6.73 (s, 2H Ar), 5.065 (t, 2H OH), 4.46 (d, 4H CH$_2$OH), 3.87 (s, OCH$_3$);
$^{13}$C NMR: δ 151.14 (Ar—C), 149.67 (Ar—C), 128.81 (Ar—C), 127.36 (Ar—C), 120.94 (Ar—C), 108.59 (Ar—C), 63.78 (CH$_2$OH), 55.32 (OCH$_3$).

Example 9: Preparation of Compound (9)

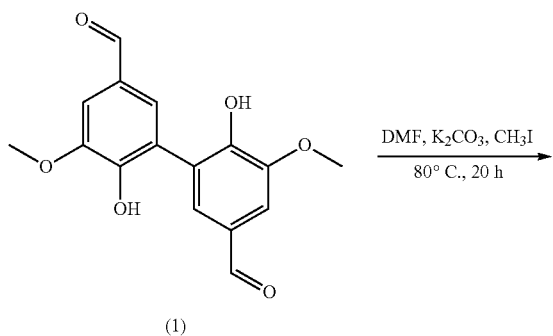

methylated divanillin (9)

26 mmol of divanillin (≈8 g) were dissolved in 120 mL of DMF. 15.2 g of potassium carbonate (110 mmol) were added before a slow addition of 9.6 mL of iodomethane (158 mmol). After 15 h of stirring at 80° C., the mixture was filtered and the resulting solution poured into cold water. The methylated compound which precipitated was filtered off and dried under vacuum. Yield: 80%.

Analyses:
$^1$H NMR: δ 9.94 (s, CHO), 7.58 (s, 2H Ar), 7.55 (s, 2H Ar), 3.95 (s, OCH$_3$), 3.68 (s, OCH$_3$);
$^{13}$C NMR: δ 191.83 (CHO), 152.80 (Ar—C), 151.21 (Ar—C), 131.90 (Ar—C), 131.58 (Ar—C), 125.96 (Ar—C), 111.14 (Ar—C), 60.47 (OCH$_3$), 55.93 (OCH$_3$).

Example 10: Preparation of Compound (10)

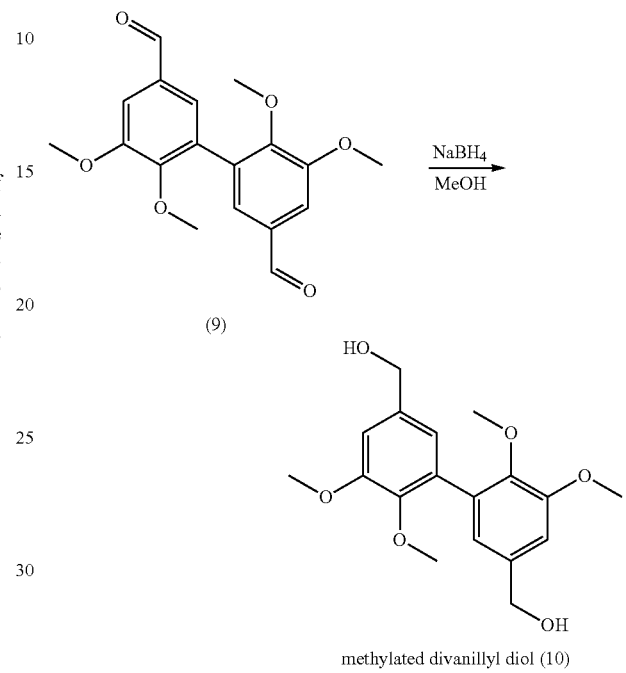

methylated divanillyl diol (10)

20 mmol of methylated divanillin (≈6 g) were dissolved in 100 mL of ethanol.

The flask was put in an ice bath and 3.6 g of sodium borohydride (100 mmol) were added slowly. Then the mixture was stirred at room temperature for 30 min. 45 mL of water were added to stop the reaction and the solution is acidified with HCl to pH 7 and warmed for 5 min at 50° C. The solvent was evaporated; the resulting solid is was solubilized in dichloromethane and washed 3 times with water. Yield: 85%.

Analyses:
$^1$H NMR: δ 6.99 (s, 2H Ar), 6.67 (s, 2H Ar), 5.15 (t, 2H OH), 4.47 (d, 4H CH2OH), 3.83 (s, OCH$_3$), 3.51 (s, OCH$_3$);
$^{13}$C NMR: δ 151.93 (Ar—C), 144.86 (Ar—C), 137.52 (Ar—C), 132.14 (Ar—C), 120.27 (Ar—C), 110.20 (Ar—C), 62.69 (CH$_2$OH), 59.83 (OCH$_3$), 55.53 (OCH$_3$).

Example 11: Preparation of Compound (11)

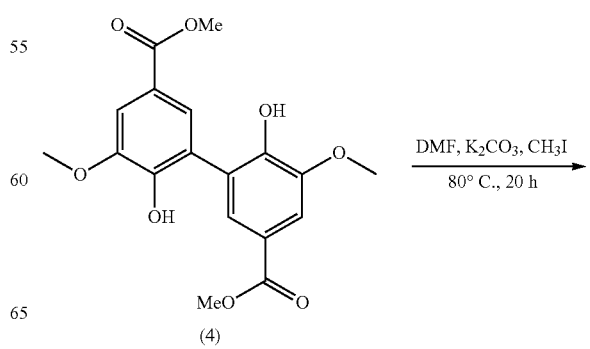

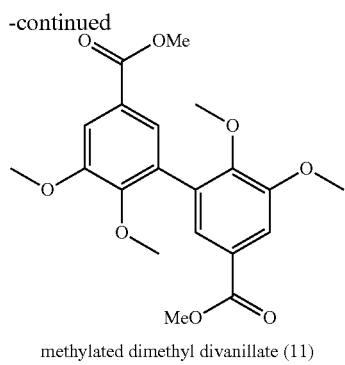

methylated dimethyl divanillate (11)

26 mmol of dimethyl divanillate (≈8 g) were dissolved in 120 mL of DMF. 15.2 g of potassium carbonate (110 mmol) were added before a slow addition of 9.6 mL of iodomethane (158 mmol). After 15 h of stirring at 80° C., the mixture was filtered and the resulting solution poured into cold water. The methylated compound which precipitated was filtered off and dried under vacuum. Yield: 80%.

Analyses:
$^1$H NMR: δ 7.59 (s, 2H Ar), 7.41 (s, 2H Ar), 3.92 (s, OCH$_3$), 3.84 (s, OCH$_3$), 3.62 (s, OCH$_3$);
$^{13}$C NMR: δ 165.63 (OCH$_3$ester), 152.16 (Ar—C), 149.95 (Ar—C), 131.19 (Ar—C), 124.44 (Ar—C), 123.81 (Ar—C), 112.43 (Ar—C), 60.38 (OCH$_3$), 55.73 (OCH$_3$ ester), 52.81 (OCH$_3$).

Example 12: Preparation of Compound (12)

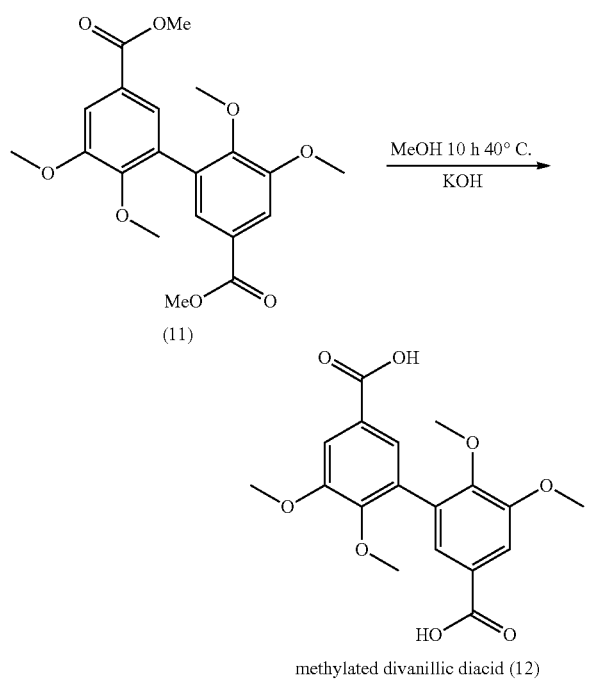

methylated divanillic diacid (12)

7 mmol of methylated dimethyl divanillate (≈2.5 g) were dissolved in 10 mL of methanol. 2.5 g of KOH (45 mmol) were added and the solution was warmed to reflux for 9 h. The reaction was stopped with 2.5 mL of water. The remaining diester is extracted with diethylether. The aqueous phase was acidified with HCl and the diacid precipitated. Yield: 94%.

Analyses:
$^1$H NMR: δ 7.63 (s, 2H Ar), 7.42 (s, 2H Ar), 3.96 (s, OCH$_3$), 3.64 (s, OCH$_3$);
$^{13}$C NMR: δ 166.72 (COOH), 152.21 (Ar—C), 149.91 (Ar—C), 131.06 (Ar—C), 123.86 (Ar—C), 112.88 (Ar—C), 59.89 (Ar—C), 55.84 (OCH$_3$), 55.86 (OCH$_3$).

Example 13: Preparation of Compound (13)

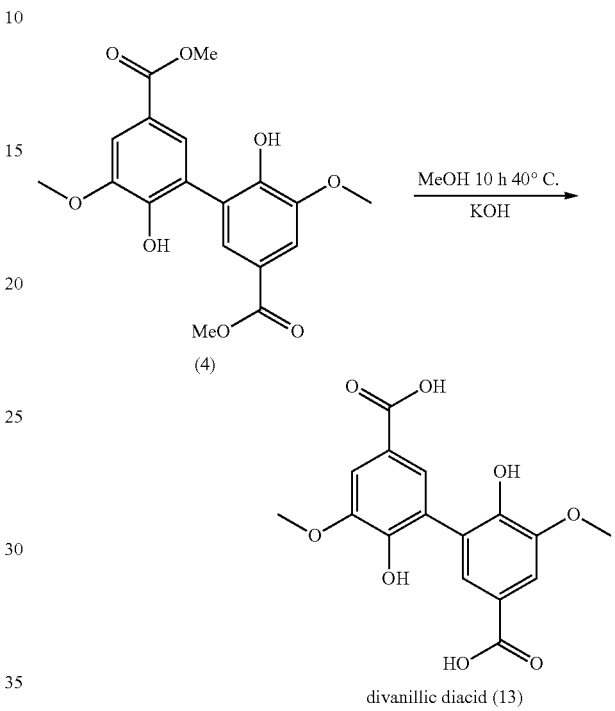

divanillic diacid (13)

7 mmol of dimethyl divanillate (≈2.5 g) were dissolved in 10 mL of methanol. 2.5 g of KOH (45 mmol) were added and the solution was warmed to reflux for 9 h. The reaction was stopped with 2.5 mL of water. The remaining diester is extracted with diethylether. The aqueous phase was acidified with HCl and the diacid precipitated. Yield: 92%.

Analyses:
$^1$H NMR: δ 7.52 (s, 2H Ar), 7.48 (s, 2H Ar), 3.96 (s, OCH$_3$);
$^{13}$C NMR: δ 166.91 (COOH), 148.20 (Ar—C), 147.24 (Ar—C), 125.23 (Ar—C), 124.06 (Ar—C), 120.66 (Ar—C), 111.20 (Ar—C), 55.84 (OCH$_3$).

Example 14: Preparation of Compound (14)

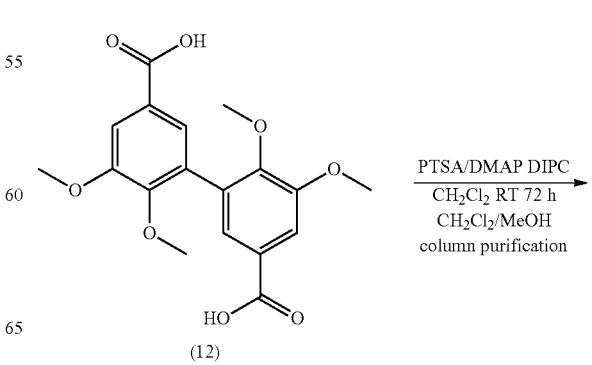

-continued

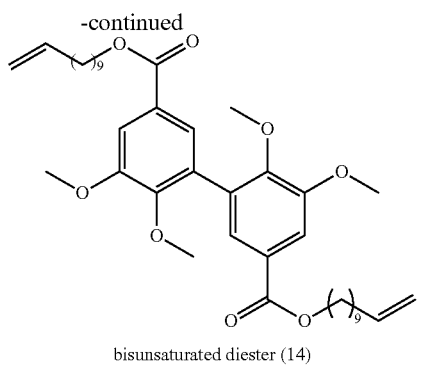

bisunsaturated diester (14)

3 g of dimethyl divanillate (16 mmol of acid functional groups) was dissolved in 80 ml of CH$_2$Cl$_2$ under stirring. Subsequently 16 mmol of p-toluene sulfonic acid/4-dimethylaminopyridine catalyst in a molar ratio 1/1.2 was added. The flask was placed in an ice bath and subsequently an excess of undecenol (4.8 mL, 24 mmol) was added to the solution. Finally, N,N'-diisopropyl carbodiimide (DIPC, 7.2 ml 46 mol) was added dropwise under stirring. The reaction was left under stirring for 72 hours at room temperature. Afterwards the solution was washed three times with water, dried and the solvent was removed under reduced pressure. The product was a yellow brown viscous liquid. The acylurea formed was eliminated by filtration after dissolution of the product in toluene. The remaining reactants were eliminated by silica column purification using dichloromethane. Yield: 60%

Analyses:
$^1$H NMR: δ 7.37 (s, 2H Ar), 7.58 (s, 2H Ar), 4.92 (m, 3H CH—CH$_2$), 4.25 (t, 2H CH$_2$—COO), 3.92 (s, OCH$_3$), 3.62 (s, OCH$_3$), 1.97 (m, 3H—CH$_2$—), 1.67 (m, 2H—CH$_2$—), 1.23 (m, 13H—CH$_2$—);
$^{13}$C NMR: δ 164.84 (COO), 152.12 (Ar—C), 150.30 (Ar—C), 138.56 (C=C), 131.26 (Ar—C), 125.08 (Ar—C), 123.50 (Ar—C), 114.34 (C=C), 112.55 (Ar—C), 64.59 (OCH$_2$), 60.23 (OCH$_3$), 56.06 (OCH$_3$), 25.40-32.99 (CH$_2$).

Example 15: Preparation of Compound (15)

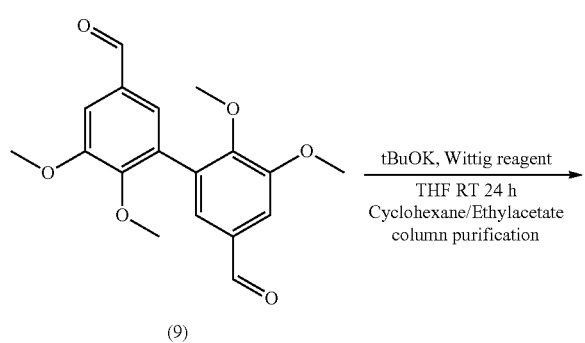

Divinyl Synthesis: Wittig Reaction (15)

3 g of triphenylphosphine (11.4 mmol) were dissolved in 30 mL of toluene. 0.7 mL of iodomethane (11.4 mmol) was added dropwise. The mixture is stirred to reflux at 120° C. under nitrogen flow. Methyltriphosphoniumiodide precipitated and was filtered off and dried under vacuum.

To a solution of methyltriphosphoniumiodide (8.8 g, 22 mmol) in dry THF (36 mL), 2.7 g of potassium tert-butoxide were added at 0° C. After 1 h of stirring at room temperature under nitrogen, 3.2 g of divanillin (10 mmol) was added. The mixture is stirred at 35° C. for 24 h. The solution is diluted with 75 mL of dichloromethane, washed with water and 2 times with brine. The solvent of the organic phase is evaporated. The remaining reactants were eliminated by silica column purification using dichloromethane/cyclohexane 50/50. Yield: 75%

Analyses:
$^1$H NMR: δ 7.17 (s, 2H Ar), 6.83 (s, 2H Ar), 6.70 (q, 2H CH—CH$_2$), 5.77 (d, 2H CH—CH$_2$), 5.19 (d, 2H CH—CH$_2$), 3.87 (s, OCH$_3$), 3.53 (s, OCH$_3$);
$^{13}$C NMR: δ 152.34 (Ar—C), 145.84 (Ar—C), 136.25 (CH—CH$_2$), 132.66 (Ar—C), 132.01 (Ar—C), 120.82 (Ar—C), 113.30 (CH—CH$_2$), 109.25 (Ar—C), 59.94 (OCH$_3$), 55.53 (OCH$_3$).

Example 16: Preparation of Compound (16)

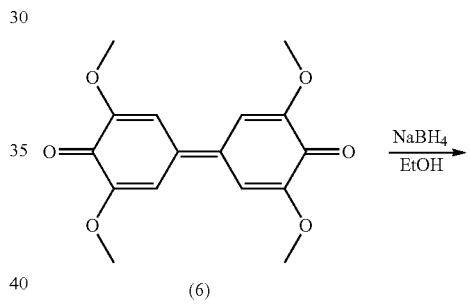

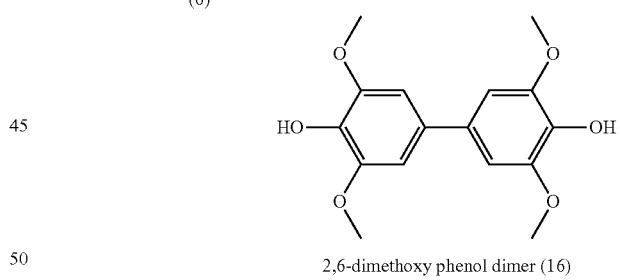

2,6-dimethoxy phenol dimer (16)

6 g of 2,6-dimethoxy phenol dimer (20 mmol) were dissolved in 180 mL of ethanol. The flask was put in an ice bath and 6.75 g of sodium borohydride (178 mmol) were added slowly. Then the mixture was stirred at room temperature for 30 min. 80 mL of water were added to stop the reaction and the solution is acidified with HCl to pH 7 and warmed for 5 min at 50° C. The solvent was evaporated; the resulting solid was solubilized in dichloromethane and washed 3 times with water. Yield: 78%.

Analyses:
$^1$H NMR: δ 8.34 (s, 1H OH), 6.88 (s, 2H Ar), 3.90 (s, OCH$_3$);
$^{13}$C NMR: δ 148.13 (Ar—C), 134.98 (Ar—C), 131.00 (Ar—C), 104.12 (Ar—C), 55.98 (OCH$_3$).

Example 17: Preparation of Compound (17)

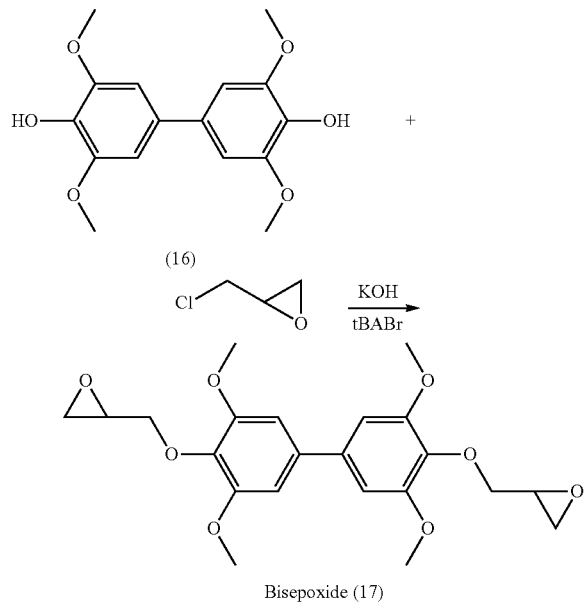

Bisepoxide (17)

5 g of reduced 2,6-dimethoxy phenol dimer (16 mmol) were dissolved in 16 mL of epichlorohydrin. 7.9 g of potassium hydroxide (141 mmol) and 1 g of tetrabutylammonium bromide (3.1 mmol) were added and the solution is stirred at room temperature for 4 h. The product is extracted with dichloromethane and washed with water. Dichloromethane and epichlorohydrin are removed from the organic phases under vacuum. Yield: 95%.

Analyses:

$^1$H NMR: δ 6.89 (s, 2H Ar), 4.11 (dd, 1H OCH$_2$), 3.87 (s, OCH$_3$), 3.76 (q, 1H OCH$_2$), 2.74 (t, CH), 2.60 (q, CH$_2$ epoxy), 2.50 (q, CH$_2$ epoxy);

$^{13}$C NMR: δ 152.73 (Ar—C), 136.37 (Ar—C), 135.84, 104.81 (Ar—C), 173.55 (OCH$_2$), 56.03 (OCH$_3$), 50.11 (CH epoxy), 43.02 (CH$_2$ epoxy).

Example 18: Preparation of Compound (18)

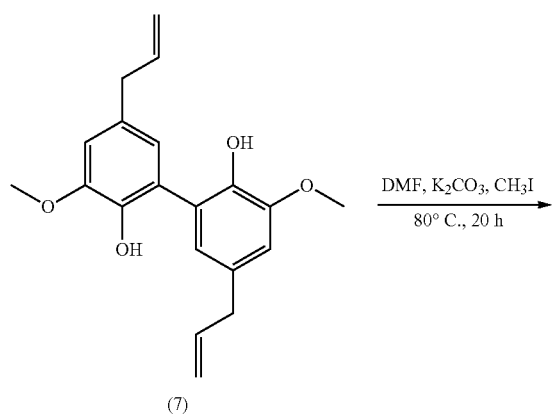

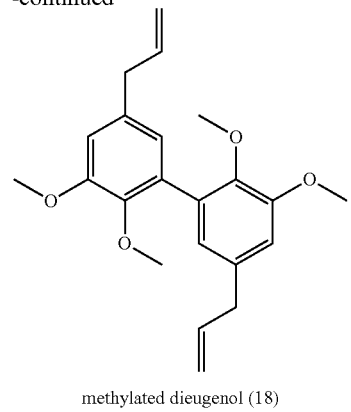

methylated dieugenol (18)

26 mmol of bisphenol compound (7) (≈8 g) were dissolved in 120 mL of DMF. 15.2 g of potassium carbonate (110 mmol) were added before a slow addition of 9.6 mL of iodomethane (158 mmol). After 15 h of stirring at 80° C., the mixture was filtered and the resulting solution poured into cold water. The methylated compound which precipitated was filtered off and dried under vacuum. Yield: 85%.

Analyses:

$^1$H NMR: δ 6.93 (s, 2H Ar), 6.61 (s, 2H Ar), 6.03 (q, 2H CH—CH$_2$), 5.13 (d, 4H CH—CH$_2$), 3.89 (s, OCH$_3$), 3.56 (s, OCH$_3$), 3.42 (d, 2H CH$_2$);

$^{13}$C NMR: δ 152.02 (Ar—C), 144.15 (Ar—C), 137.53 (CH—CH$_2$), 134.73 (Ar—C), 132.29 (Ar—C), 122.19 (Ar—C), 115.77 (Ar—C), 112.15 (CH—CH$_2$), 59.80 (OCH3), 55.44 (OCH$_3$), 39.29 (CH$_2$).

Example 19: Preparation of Compound (19)

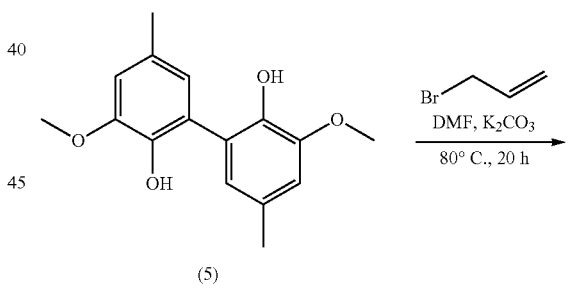

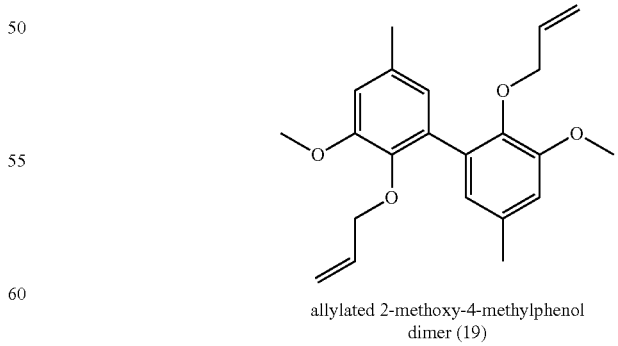

allylated 2-methoxy-4-methylphenol dimer (19)

26 mmol of 2-methoxy-4-methoxyphenol dimer were dissolved in 120 mL of DMF. 15.2 g of potassium carbonate (110 mmol) were added before a slow addition of 19.1 g of allylbromide (156 mmol). After 15 h of stirring at 80° C., the mixture was filtered and the resulting solution poured into cold water. The methylated compound which precipitated was filtered off and dried under vacuum. Yield: 50%.

Analyses:

$^1$H NMR: δ 6.84 (s, 2H, Ar), 6.55 (s, 2H, Ar), 5.70 (m, 2H, CH=CH$_2$), 4.99 (dd, 4H, CH=CH$_2$), 4.21 (d, 4H, OCH$_2$), 3.80 (s, 6H, OCH$_3$), 2.26 (s, 6H, CH$_3$);

$^{13}$C NMR: δ 151.98 (Ar—C), 142.92 (Ar—C), 134.95 (CH=CH$_2$), 13.30 (Ar—C), 132.17 (Ar—C), 123.03 (Ar—C), 116.43 (CH=CH$_2$), 112.67 (Ar—C), 73.21 (CH$_2$), 55.36 (OCH$_3$), 20.78 (CH$_3$).

The invention claimed is:

1. A process for preparing a compound having the formula (2):

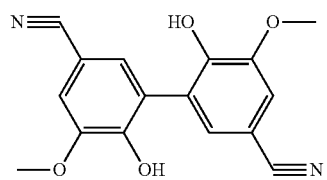

said process comprising:
a) the addition of an oxygen source into a solution of a compound of formula (II-1) in a water-miscible solvent, said compound of formula (II-1) having the following formula:

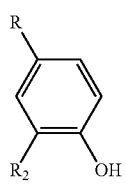

wherein R is —CN and R$_2$ is methyl;
b) the addition of a laccase into said solution; and
c) recovering the compound of formula (2).

2. The process of claim 1, wherein the water-miscible solvent is acetone.

3. The process of claim 1, wherein the laccase is from *Trametes versicolor*.

4. The process of claim 1, wherein the amount of laccase for one gram of compound of formula (II-1), is from 1.5 mg to 75 mg.

5. The process of claim 1, wherein the solution of the compound of formula (II-1) in a water-miscible solvent is prepared by adding said compound of formula (II-1) in said water-miscible solvent, and adding a buffer solution.

6. The process according to claim 5, wherein the amount of water-miscible solvent is comprised between 5% and 10% of volume in comparison with the total volume of the mixture formed by said solvent and the buffer solution.

7. The process of claim 1, wherein the addition of an oxygen source is carried out for a sufficient time to saturate the solution in dissolved oxygen.

8. The process of claim 1, wherein the solution of the compound of formula (II-1) in the water-miscible solvent is saturated in oxygen.

9. The process of claim 1, wherein the pH of the solution of the compound of formula (II-1) in the water-miscible solvent is comprised between 4 and 7.

10. A process for the preparation of a compound having the following formula (14):

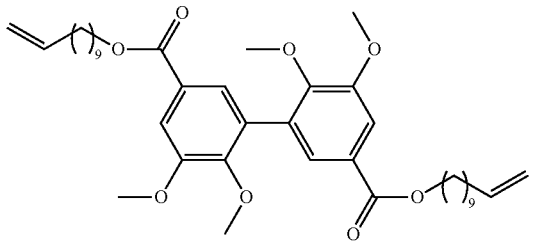

said process comprising:
a) reacting a compound of formula (V), said compound having the following formula:

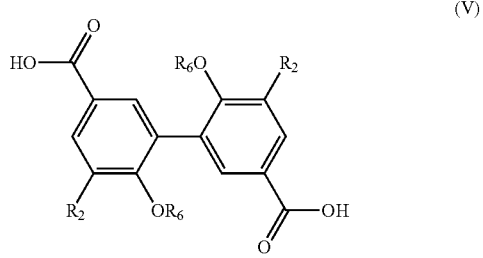

wherein R$_2$ is OMe and R$_6$ is methyl;
with an alcohol formula R$_7$OH, wherein R$_7$ is a (CH2)$_9$—CH=CH2, in the presence of a catalyst and N,N'-diisopropyl carbodiimide; and
b) recovering the compound of formula (14).

11. A process for the preparation of a compound having the following formula (15):

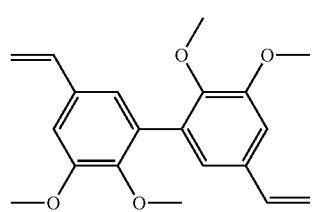

said process comprising:
alkylating the compound of formula (I-1), said compound having the following formula:

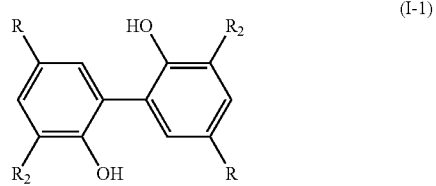

wherein R is CHO and $R_2$ is methyl with a compound $R_8X$, X being a halogen, to obtain a compound having the following formula (III-1):

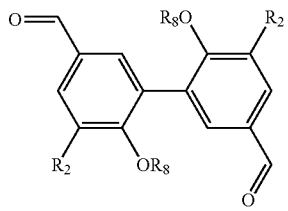

(III-1)

wherein $R_2$ is methyl and $R_8$ is methyl,
reacting the compound of formula (III-1) with a Wittig reagent, in order to obtain a compound having the formula (15),
and recovering the compound of formula (15).

12. A process for the preparation of a compound having the following formula (19):

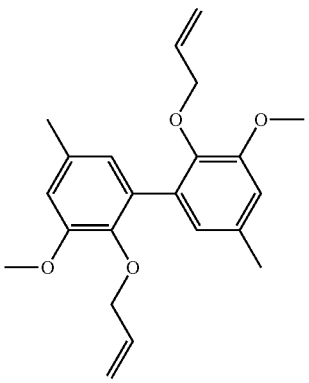

(19)

said process comprising:
reacting the compound of formula (I-1), said compound having the following formula:

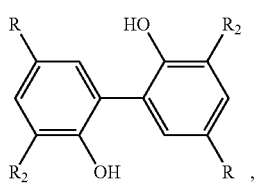

(I-1)

wherein R is methyl and $R_2$ is methyl, with a compound $R_9X$, wherein $R_9$ is CH2-CH=CH2 and X is a halogen, in the presence of $K_2CO_3$ in a solvent; and recovering the compound of formula (19).

13. A compound having one of the following formulae:

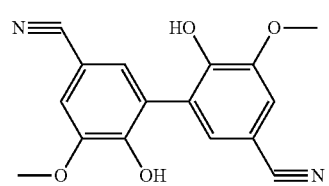

(2)

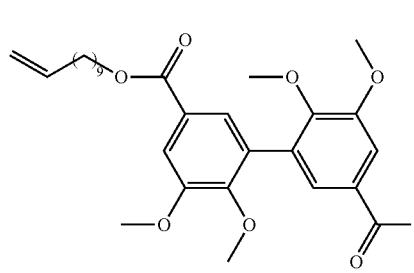

(14)

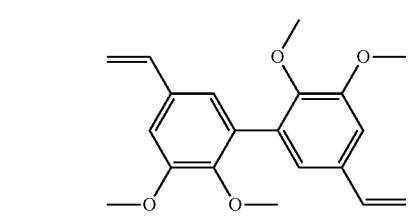

(15)

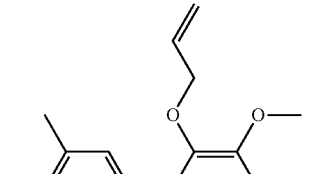

(19)

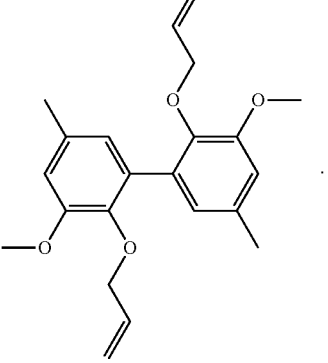

* * * * *